(12) United States Patent
Gregory et al.

(10) Patent No.: US 12,298,118 B2
(45) Date of Patent: *May 13, 2025

(54) METHOD AND SYSTEM FOR MEASURING COATING THICKNESS

(71) Applicant: TeraView Limited, Cambridge (GB)

(72) Inventors: Ian Stephen Gregory, Cambridge (GB); Robert May, Cambridge (GB); Daniel James Farrell, Cambridge (GB)

(73) Assignee: TeraView Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,561

(22) Filed: Dec. 12, 2023

(65) Prior Publication Data

US 2024/0167810 A1 May 23, 2024

Related U.S. Application Data

(63) Continuation of application No. 17/352,766, filed on Jun. 21, 2021, now Pat. No. 11,885,610, which is a
(Continued)

(30) Foreign Application Priority Data

Jan. 27, 2017 (GB) .................................. 1701405

(51) Int. Cl.
*G01B 11/06* (2006.01)
*G01N 21/3581* (2014.01)
*G01N 33/32* (2006.01)

(52) U.S. Cl.
CPC ..... *G01B 11/0625* (2013.01); *G01N 21/3581* (2013.01); *G01N 33/32* (2013.01)

(58) Field of Classification Search
None
See application file for complete search history.

(56) References Cited

U.S. PATENT DOCUMENTS 5,099,504 A 3/1992 Pettit
5,523,840 A * 6/1996 Nishizawa ......... G01B 11/0625
356/497
(Continued)

FOREIGN PATENT DOCUMENTS

DE 10 2015 107 616 A1 11/2016
EP 2 899 498 A1 7/2015
(Continued)

OTHER PUBLICATIONS

K. Su et al., "Terahertz Sensor for Non-Contact Thickness and Quality Measurement of Automobile Paints of Varying Complexity", IEEE Transactions on Terahertz Science and Technology, vol. 4, No. 4, Jul. 1, 2014 pp. 432-439.
(Continued)

*Primary Examiner* — Marcus H Taningco
(74) *Attorney, Agent, or Firm* — Blank Rome LLP

(57) ABSTRACT

A method for determining the thickness of a plurality of coating layers. The method comprises the steps of performing a calibration analysis on calibration data to determine initial values and search limits of optical parameters of the plurality of coating layers, irradiating the plurality of layers with a pulse of THz radiation in the range from 0.01 THz to 10 THz, detecting the reflected radiation to produce a sample response derived from the reflected radiation, producing a synthesized waveform using the optical parameters and predetermined initial thicknesses of the layers, varying the thicknesses and the optical parameters within the search limits to minimize the error measured between the sample response and the synthesized waveform, and outputting the thicknesses of the layers.

22 Claims, 17 Drawing Sheets

Related U.S. Application Data continuation of application No. 16/480,186, filed as application No. PCT/GB2018/050242 on Jan. 26, 2018, now Pat. No. 11,085,755.

(56) References Cited

U.S. PATENT DOCUMENTS

| | | | |
|---|---|---|---|
| 6,573,999 B1* | 6/2003 | Yang | G01B 11/0625 356/630 |
| 7,876,423 B1* | 1/2011 | Roth | G01N 21/3581 356/27 |
| 8,665,423 B2 | 3/2014 | Withers et al. | |
| 10,076,261 B2 | 9/2018 | Arnone | |
| 11,085,755 B2 | 8/2021 | Gregory | |
| 2002/0097832 A1 | 7/2002 | Kaiser | |
| 2002/0164217 A1 | 11/2002 | Peterson | |
| 2013/0204577 A1 | 8/2013 | Savard et al. | |
| 2013/0279654 A1 | 10/2013 | Kantonen | |
| 2014/0239181 A1 | 8/2014 | Hattori | |
| 2015/0060673 A1 | 3/2015 | Zimdars | |
| 2015/0211934 A1 | 7/2015 | Van Mechelen et al. | |
| 2015/0211989 A1 | 7/2015 | Van Mechelen | |
| 2015/0212060 A1 | 7/2015 | Van Mechelen et al. | |
| 2017/0023469 A1 | 1/2017 | Zimdars | |
| 2018/0292326 A1 | 10/2018 | Manassen | |
| 2019/0041200 A1 | 2/2019 | Saeedkia | |
| 2019/0078873 A1* | 3/2019 | Saeedkia | G01S 13/10 |
| 2020/0240909 A1 | 7/2020 | Maas | |

FOREIGN PATENT DOCUMENTS

| | | |
|---|---|---|
| JP | 2015-161650 A | 9/2015 |
| WO | WO 2015/073807 A1 | 5/2015 |
| WO | WO 2016/138935 A1 | 9/2016 |
| WO | WO 2017/173533 A1 | 10/2017 |

OTHER PUBLICATIONS

I. Gregory et al., "Extending Terahertz Paint Thickness Measurements to Advanced Industry-Standard Automotive Paint Structures", 2016 41st International Conference on Infrared, Millimeter, and Terahertz Waves, IEEE, Sep. 25, 2016, p. 1.

T. Iwata et al., "Prediction of the Thickness of a Thin Paint Film by Applying a Modified Partial-Least-Squares-1 Method to Data Obtained in Terahertz Reflectometry", Journal of Infrared, Millimeter and Terahertz Waves, vol. 34, No. 10, Oct. 1, 2013, pp. 646-659.

V. Feige et al., "Berührungslose Mehrlagen-Schichtdickenmessung Industrieller Beschichtungen Mittels Thz-Messtechnik", Technisches Messen TM., vol. 79, No. 2, Feb. 1, 2012, pp. 87-94.

S. Krimi et al., "Highly accurate thickness measurement of multilayered automotive paints using terahertz technology", Appl. Phys. Lett. 109, 021105 (2016).

Krimi et al., "Advanced GPU-Based Terahertz Approach for In-Line Multilayer Thickness Measurements", IEEE Journal of selected topics in quantum electronics, vol. 23, No. 4, Jul./Aug. 2017, published on Dec. 29, 2016.

S. Krimi, "Non-Destructive Terahertz Sensor for In-line Contactless Thickness Measurement and Quality Control of Multilayered Structures" (Dissertation in German) Technical University of Kaiserslautern, ISBN: 978-3-8439-2653-9, 2016.

S. Krimi, Extract from the electronic register of the University Library of the Technical University of Kaiserslautern (Extract of Dissertation in German) Technical University of Kaiserslautern, ISBN: 978-3-8439-2653-9, 2016.

* cited by examiner

Test 1

Test 2

Test 4

Terahertz and Thickness Data

{T,X} Terahertz-Thickness Measurement Set: $M$ terahertz measurements $T = \{t_1, t_2 \ldots t_M\}$ from coated samples with $N$ expected (known) layer thickness combinations $X = \{x_1, x_2 \ldots x_N\}$

{T,X} Terahertz-Thickness Measurement Subset: Subset of $m$ terahertz measurements $T = \{t_1, t_2 \ldots t_m\}$ from corresponding coated samples with subset of $n$ expected (known) layer thickness combinations $X = \{x_1, x_2 \ldots x_n\}$

{$t_i,x_j$} Terahertz-Thickness Measurement Pair: single terahertz measurement $t_i$ (drawn from subset $T$) from sample with expected (known) layer thickness combination $x_j$ (drawn from subset $X$)

{S,P} Simulated Terahertz-Thickness Set: $M$ simulated terahertz measurements $S = \{s_1, s_2 \ldots s_M\}$, with corresponding predicted thickness set $P = \{p_1, p_2 \ldots\}$, produced using calibration $C$ to simulate terahertz measurement set $T$

Fig. 9(b)

Algorithmic operators (that relate measured/simulated data to calibrations)

g generator: creates output calibration $C_{out}$ from input calibration $C_{in}$ for sample-specific input data (measured terahertz-thickness pair)

E evaluator: evaluates calibration $C$ by comparing predicted thickness set $P$ (corresponding to simulated terahertz measurements $S$ generated for terahertz measurements $T$) with expected thickness set $X$

O optimiser: uses numerical optimisation to find best-fit simulation(s) to measured terahertz measurement(s) by modifying parameters of calibration $C$ that describe thickness and optical properties of layer(s) and possibly a non-metal substrate

D Difference quantifier: operation to quantify differences between simulations and terahertz measurements, including differences between predicted and expected layer thickness values

Fig. 9(c)

| Terminology relating to calibrations | |
|---|---|
| C | generic calibration: mathematical description of (thickness and terahertz optical properties of) single- or multi-layer coated substrate |
| Q | quality metric: scalar quantity representing how well calibration C accurately minimises differences between predicted (P) and expected thicknesses (X) for terahertz measurement set T, while simultaneously minimising residuals between terahertz measurements T and simulations S |
| S | single-layer calibration (for coating or substrate) |
| M | multi-layer calibration (combining single-layer calibrations) |

Fig. 9(d)

METHOD AND SYSTEM FOR MEASURING COATING THICKNESS

CROSS-REFERENCE TO RELATED APPLICATIONS

This is a continuation of U.S. application Ser. No. 17/352,766, filed Jun. 21, 2021, which is a continuation of U.S. application Ser. No. 16/480,186, filed Jul. 23, 2019, now U.S. Pat. No. 11,085,755, which is national stage of PCT/GB2018/050242, filed Jan. 26, 2018, which claims priority to United Kingdom Application No. 1701405.1, filed Jan. 27, 2017, the entire disclosures of which are incorporated by reference herein.

FIELD OF THE INVENTION

Embodiments of the present invention relate to the field of measuring coatings using terahertz radiation.

BACKGROUND

Terahertz radiation is a non-invasive method of determining the internal structure of an object and the thickness of its layers.

For a coated substrate consisting of coatings (and substrate) of known thickness and optical response, as described by the refractive index of each material (coatings and substrate), the terahertz time-domain waveform reflected from such a stack of thin films can be calculated rapidly using a matrix formalism of Fresnel equations.

The inverse problem of determining the optical response and/or thickness of the coating(s) and/or substrate from a known (measured or simulated) reflection cannot, like most inverse problem, be solved directly by analytical means but instead requires a numerical approach in which different combinations of the system parameters (thickness and optical response) are tested until a combination is found that results in a good match between the corresponding calculated signal and the known signal. Numerical optimisation techniques can be employed to efficiently search the multi-dimensional solution space to find a combination that minimizes, in a least squares sense, the difference between simulated and known signals.

The problem of unambiguously determining the values of unknown coating properties (thickness and/or refractive index) is made difficult because the information content of the terahertz signal reflected from a stack of coatings is limited because 1) the thickness of individual relevant coatings (e.g. automotive or aircraft paint layers) can be on the scale of or indeed below the wavelength of the incident terahertz light; and 2) neighbouring coating layers may exhibit limited contrast (in terms of the refractive index of each coating material). The first consideration means that the material refractive index determined from a thick sample of a material may not be representative of the refractive index of the same material applied at a lower thickness.

This problem becomes more acute when considering coating techniques that use so-called a "wet on wet" application process where the next layer is applied before the previous layer has been completely cured or dried. This may result in significant intermixing of the layers at the boundaries affecting both the thickness of the layers, the roughness of the interfaces and also the optical properties of the layers at their interfaces.

BRIEF DESCRIPTION OF THE DRAWINGS

Embodiments of the invention will now be described, by way of example, only with reference to the accompanying schematic drawings in which:

FIGS. 9(b) to 9(d) are panels defining various operators and concepts used in diagrams 9(c) to 9(i);

DETAILED DESCRIPTION

Figure 1:
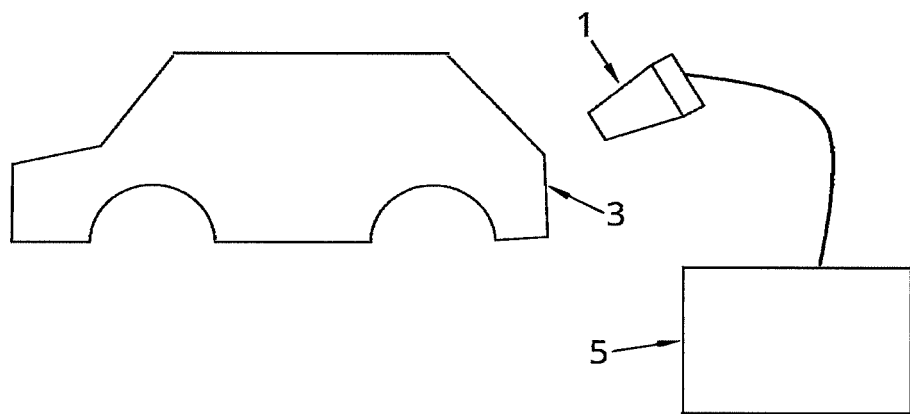
FIG. 1 is an overview of a general system in accordance with an embodiment of the invention.

In an embodiment a method for determining the thickness of a plurality of coating layers is provided, the method comprising:
 performing a calibration analysis on calibration data to determine initial values and search limits of optical parameters of the plurality of coating layers,
 irradiating the plurality of layers with a pulse of THz radiation, the pulse comprising a plurality of frequencies in the range from 0.01 THz to 10 THz;
 detecting the reflected radiation to produce a sample response derived from the reflected radiation;
 producing a synthesized waveform using the optical parameters and predetermined initial thicknesses of the layers; and varying the thicknesses and varying the optical parameters within the search limits to minimize the error measured between the sample response and the synthesized waveform; and outputting the thicknesses of the layers.

The above embodiment allows the problem of determining best-fit parameters values to synthesize a THz waveform to be simplified if the dimension and size of the solution space to be explored (by least squares minimisation) can be reduced, by applying constraints (and/or upper and lower bounds) on the possible values for the unknown quantities (thickness and refractive index). The problem of calculating individual coating thickness is greatly reduced if the optical response (refractive index) of all coatings and substrate are known in advance. Thus, given the optical properties (defined by initial values and upper/lower bounds on refractive index model parameters that may produce a constrained, but not necessarily fixed, refractive index) of each coating and the measured reflected signal, the thickness of individual coating layers can be calculated using a local optimisation routine to minimize the difference between the measured and simulated signals.

This allows reduced processing time with an accurate result that can be output for each layer and which can cope with variations in temperature and other conditions, present when the coatings were deposited, that, if not accounted for, would otherwise cause variations in the underlying parameters and models used to predict the thickness of the layers.

In an embodiment, during the calibration phase it is possible for the system to determine that the search limits of one or more of the optical parameters are zero. In this case, for the optical parameters with zero search limits, the optical parameters remain constant during the fitting of the sample data.

In an embodiment, the calibration analysis comprises selecting preferred refractive index models from data from a first set of calibration samples and determining initial values and search limits of optical parameters from data from a second set of calibration samples. Here, the first set of calibration samples may be samples with a substrate and a single coating layer and the second set of calibration samples may have a substrate and the said plurality of coating layers.

In an embodiment, the first set of samples and the second set of samples may be provided on separate substrates to each other and also to the layers which are to be analyzed. In a further embodiment, the said plurality of coating layers are provided on an object and second set of calibration samples are areas of the said object different from the area where the THz radiation is used to measure the said plurality of coating layers. For example, if the object is a vehicle, the second set of calibration samples may be a different part or area of the vehicle to the part that is to be analysed.

In an embodiment, the method further comprises measuring a set of calibration samples using THz radiation in the range 0.01 THz to 10 THz, and making a time domain measurement of the reflected radiation to produce said data. The calibration analysis may comprise receiving calibration data comprising a time domain measurement of THz radiation in the range 0.01 THz to 10 THz reflected from the said calibration samples and fitting a synthesized waveform to said data.

For the second set of calibration samples, the fitting parameters for the synthesized waveform may comprise the optical parameters and the thickness of the layers. For the second set of calibration samples, the thickness of the layers may be measured by a modality other than a THz measuring system, e.g. optical microscopy, ultrasound etc. However, the fitting of the second calibration data assumes that there is an error in these measured thicknesses and therefore allows them to vary during the fitting of the second calibration data.

In summary, the calibration model treats external measurements as approximate and finds the optical model which best fits the calibration measurements within the approximate thicknesses of the alternative modality. Here 'external measurements' and 'alternative modality' refer to thickness measurements made by independent means (e.g. ultrasonic thickness gauge or preferably optical microscopy). Independent measurements of individual coating layer thickness are made on both sets of panels used for calibration: single-layer panels and multi-layer panels. The thickness measurements are used to guide the minimisation search routines used by both single-layer and multi-layer calibration routines in order 1) to determine the optimum model to describe the refractive index of each coating layer and 2) to determine the initial values and search ranges of each parameter of said optical models.

Single-layer calibration utilises a global optimisation search routine that requires upper and lower bounds to be defined for all model parameters (optical models and layer thicknesses). The global search routine tests combinations of parameter values that starts by generating random values that lie within these upper/lower bounds. A total thickness gauge (e.g. Elcometer) can be used for single-layer panels, since only one coating is present on these panels. Furthermore, since a search range is placed on the thickness of the individual coating layer in the global optimisation routine, the measured thickness of single-layer panels need not be as accurate as measurements of individual coating layers made on multi-layer panels.

For multi-layer panels a measurement technique that can measure the individual thickness of all coating layers, rather than the total coating thickness alone, is required. The most accurate and direct means is by optical microscopy made on cross-sectioned pieces of the multi-layer panel. Any measurement technique will have an inherent uncertainty associated with thickness measurements, therefore the values provided even by optical microscopy may not reflect the thickness at the exact location where terahertz measurements were made. Multi-layer calibration uses a local optimisation search routine to find the set of model parameter values (and search ranges) that can produce coating thicknesses that best match the independently measured coating thicknesses. The local search routine is initialised by setting the coating thicknesses to those values provided by independent measurements. Because of the uncertainty that exists on independent thickness measurements, the coating thickness parameters are permitted to deviate during local optimisation by an amount determined by the uncertainty of independent thickness measurements.

Order of Terahertz Measurements and Independent Thickness Measurements

Despite attempts to produce coated panels in which the individual coating layers have uniform thickness, natural thickness variations across a coated panel means that it is essential that the terahertz point measurement and independent thickness measurements are performed in the same location. Given that optical microscopy is a destructive technique, this implies that terahertz measurements must be made before the panels are sectioned for optical microscopy can be performed. Additionally, total thickness measurements of single-layer panels using a sensor with a probe (e.g. Elcometer) that makes contact with the painted surface may deform the surface of the coated layer, therefore (non-contact) terahertz measurements should be made before (in-contact) independent thickness measurements are made.

Using the above, the multi-layer calibration uses individual layer calibrations as a start point but which allows the optical properties to vary to find the best calibration for the full stack, the variations allowing for Potentially different properties of the actual stack including some intermingling due to wet-on-wet or other differences from the single layer samples The fact that layers are thin and can be considerably thinner than the wavelength The description of optical properties of single-layer panels, as provided by single-layer calibration routine, include the type of model (e.g. Debye or Drude-Lorentz) that is best suited to describe the refractive index of the coating material as well as the best-fit values (and uncertainties) on the parameters that define the selected model for the measurement of the single-layer panel. The results of single-layer calibration for each coating present in a multi-layer calibration panel are combined and referred to as the initial multi-layer calibration. The multi-layer calibration routine seeks to find a set of optimum model parameter values (including uncertainties) that best describe reflection from multi-layer calibration panels (that, ideally, are produced on the same production line where vehicle coatings are applied) and that replicate the expected thicknesses (as measured by independent means) of the individual coating layers present on the multi-layer calibration panels. The optical model parameter values provided by single-layer calibration therefore act as the starting point from which the local optimisation routine of the multi-layer calibration routine begins. These values, that describe the complex-valued refractive index profile of each coating material, can change from the initial values for a variety of reasons: a) the sub-wavelength thickness of the coatings mean that refractive index is somewhat thickness dependent and because the thickness of single-layer coatings panels may differ from those on the multi-layer panels, so too might the refractive index; b) the top and bottom surfaces each coating may not be well defined due to surface and/or interfacial roughness, and/or because of intermixing between adjacent coating layers, particularly in the case of wet-on-wet coating applications.

As explained above, when fitting the layer thicknesses of the sample measurement, the thickness calculation is based on the estimated multi-layer properties but the fitting allows them to vary within narrow bounds. Thus, the calculation is based on which combination of thicknesses and properties gives the best fit between the simulation and actual waveforms.

Multi-layer calibration provides initial estimates of the various parameters that describe refractive index for each coating, and also provides a search range within which those parameters are permitted to vary during the local optimisation routine that is used for coating thickness calculation. Optical parameter search limits are automatically determined based on the uncertainty of best-fit parameters during multi-layer calibration. If that search range is deemed to be excessive (if half the 95% confidence interval exceeds the best-fit parameter value) then any change in that parameter away from its best-fit value will have negligible impact on the calculated thicknesses and therefore the search range is set to zero. Such parameters with a zero search range are thus considered to be fixed parameters during future optimisation (to calculate coating thickness). Thus the refractive index profile of each coating in a multi-layer coating is permitted to vary somewhat during coating thickness calculation so as to account for changes in the effective refractive index of coating layers due, for example, to differences in coating thickness combinations and degrees of coating intermixing that occurs across the surface of a coated body.

In an embodiment, the output of the fitting of the calibration data of the first samples comprises a ranked list of the refractive models. Then, when performing the calibration on the second set of samples, the first ranked refractive model is used to fit the second calibration data, and wherein if this model produces poor results, the next refractive model from the ranked list is selected. The refractive index models may be selected from constant refractive index, Lorentz and Debye formulations of the refractive index.

As noted above, at least one of the layers of the plurality of layers may have a thickness smaller than the wavelength of the THz radiation used to measure its thickness. Also, the above method can cope when there is intermingling of the layers of the said plurality of layers at at least one of the interfaces between the said layers.

In an embodiment the sample response is derived from the reflected waveform by deconvolving the reflected waveform with the instrument response, wherein the instrument response is a measurement of the contribution of sensor components used to measure the reflected waveform. Here, the instrument response may be determined from the THz signal reflected from a mirror to produce a reference signal.

In a further embodiment the method is configured to taken an "internal reference" measurement. Such a measurement can be provided before any sample measurement as a way of continually monitoring the instrument response. Thus, in an embodiment, the mirror is a movable provided in the path of the THz beam before the focus of the THz beam, the method further comprising applying a scaling function to the instrument response measured using the movable mirror in order to mimic the instrument response as if measured by a mirror placed at the focus. The scaling function can be derived by measuring the instrument response using a mirror positioned at the focus and comparing this with the instrument response using the movable mirror. This measurement of the scaling function can be performed offline. For example, it can be performed during general maintenance of the system. However, the actual measurement of the internal reference can be performed with each sample measurement.

The position of the sample with respect to the focus of the THz radiation is likely to vary. Slight variations in distance between coated surface and focus of terahertz beams is removed from individual recorded time-domain waveforms before averaging individual waveforms to increase signal-to-noise of measured waveform. Waveform alignment is necessary to ensure the reflection features (reflection peaks and troughs that contain information relating to the optical properties and thickness of coating layers) contained in individual waveforms occur at same points in time, otherwise averaging will result in blurring of such features and loss of information related to the coating properties. Thus, in an embodiment, the method further comprises aligning the sample response and the synthesized waveform prior to fitting. This may be done for example by determining the position of the surface of the said plurality of layers from the first increase in amplitude of the sample response over a threshold level, the first increase being measured with respect to time, and aligning the position corresponding to the sample surface of the synthesized waveform with that of the sample response. However, for some samples, it may be difficult to isolate the sample surface from the sample response data. For these, the raw reflected waveform may be analyzed.

In a further embodiment the confidence levels on the thicknesses outputted are provided, said confidence levels being based on the accuracy of the fit. The output of multi-layer calibration includes uncertainties associated with the coating thicknesses calculated from the multi-layer panels used for calibration. These uncertainties can be used to represent the level of uncertainty that can be expected to be seen from coating thicknesses measured from a coated body with the same multiple coating combination. Performing a comparison between the uncertainties on calculated coating thickness with expected levels of uncertainty (provided by multi-layer calibration) allows for the identification of erroneous measurements: measurements that produce uncertainties in excess of the expected level of uncertainty can be flagged as problematic.

In a further embodiment, the method further comprises processing the sample response to compensate for changes in the angle from which the measurement was made. In one embodiment, Waveform simulation includes an additional parameter, independent of those related to the coated sample (optical properties and thicknesses of coatings), to account for a reduction in measured terahertz waveform amplitude that accompanies changes in coated surface orientation relative to the terahertz beam. In normal orientation, the reflected waveform amplitude is at a maximum, but decreases uniformly across all frequencies as the angle between terahertz beam and surface normal increases. This uniform change in waveform amplitude can be included in simulations by multiplying the simulated waveform by a constant scaling factor (with a default value of 1 at normal orientation and that decreases with increasing angle away from normal).

A handheld sensor provides less control over positioning and orientation of the sensor compared to a robotically positioned sensor. Feedback to the operator is required to indicate when the sensor is at the preferred distance and in the preferred orientation relative to the surface of the coated body. The alternative modality referred to here may include an ultrasonic distance gauge (to indicate when the sensor is close to the focus of the terahertz beam), a visible laser (to indicate when the preferred orientation between sensor and coated surface has been achieved). Visual and/or audio feedback from these modalities allow the operator to know when the sensor has been positioned close to the preferred distance and orientation relative to the coated surface. More precise information on position and orientation is provided by continuous monitoring of various properties of the continuously streamed reflected terahertz waveforms. These features may include the position and amplitude of strongest reflection to indicate if the surface is within a specified distance from the terahertz focus and if orientation is suitable to allow for collection of sufficiently high quality data. The rate of change of position and amplitude of strongest reflection indicate how fast the sensor position and orientation is changing. Data acquisition is only permitted when the sensor is sufficiently stable. A plurality of measurements of the reflected waveform from the same point on the said plurality of layers may be produced by repeating the said measurement over time. These measurements may be averaged to lower the signal to noise ratio. In a further embodiment, they are used to measure the stability of the signal by measuring the difference between successive measurements of the reflected waveform and rejecting measurements where the difference between measurements is above a threshold. The differential of the measurements with respect to time can be taken to determine the speed at which the apparatus taking the measurements is moving. In an embodiment, this can be viewed data acquisition filtering to ensure collection of high-quality data only, i.e. when sample is sufficiently close to focus; when sensor-surface orientation is within required tolerance; and when sensor is determined to be moving slowly, e.g. to avoid collection of noisy data due to vibrations.

In a further embodiment the reflected waveform is measured using a sensor, the method further comprising positioning the sensor with a measurement gauge to determine if the sensor is at a distance from the plurality of layers to allow a measurement to be performed. The sensor may also be aligned using an angular measuring gauge to determine if the angle of the sensor is sufficient to allow a measurement to be performed. The above are particularly useful if the sensor is handheld. Thus, in an embodiment, there is sensor position feedback through interrogation of signals from terahertz and additional sensors (e.g. ultrasound, laser gauge, vision system) to indicate to operator (or robot controller) when sensor-to-surface distance and orientation are acceptable for high quality data collection In further embodiments, the sensor is positioned automatically via a robot arm. Before the robot can be trained to place the sensor at a defined set of locations on a vehicle body, any differences between where the robot believes the focus of the terahertz sensor to be and the actual location of that point in 3-D space must be known and should either be accounted for or removed before subsequent positioning of the sensor is undertaken. Different scan sequences of the robot to move the sensor focal position relative to a fixed target can be performed in order to gather data (such as the position and amplitude of the strongest reflection peak) from reflected terahertz waveforms that are then provided as input to an algorithm that calculates any differences that exist between actual and expected sensor focal position.

Repeatable positioning of the sensor at a set of pre-programmed locations on the coated surface of each vehicle body to be measured is achieved using a vision system.

The locations at which the vision system must repeatedly position the sensor are programmed using an automated positioning scan mode of the sensor to ensure it is placed at suitable distance to and orientation with respect to the location where thickness measurements are to be made. In this automated scan mode, the sensor is moved by the robot until optimum distance and orientation have been achieved, which is determined by tracking various features (such as the position and height of the strongest reflection peak) of the terahertz signal reflected from the coated surface. Here, the sensor may comprise a further modality to determine the position of the sensor. A correction may be applied to the determined position of the sensor to align the position of the sensor with respect to the focus of the THz radiation. This may be achieved, for example, by measuring the reflected waveform at a plurality of different distances from the said plurality of layers, determining the position of the focus as the position of the sensor where the reflected waveforms with the largest amplitudes are measured. Thus, automated sensor positioning through pre-defined robotically driven motion routines is achieved and with feedback provided by terahertz data to ensure robotically positioned sensor is within required sensor positional tolerances Much of the above description has related to measurements at a single point. However, it is possible for a plurality of measurements to be made as a scan across the said plurality of layers. The scan may be a line scan or an area scan. These line and area scan modes can be used with a robot-mounted sensor to allow for high density mapping of a coated surface, in which the thickness over a line or area of a coated surface is mapped by moving the sensor along trajectories running parallel to the coated surface and point measurements of coating thickness made at intervals.

In certain embodiments, the said plurality of layers are provided on a vehicle body. The above method can be incorporated into a vehicle spraying production line. For such a use, the layers may comprise one or more of a clearcoat, a basecoat, a primer, an electrocoat etc.

The method may be configured to produce the thickness result after each measurement in an on-line fashion. In further embodiments, the data may be stored and the fitting of the data performed later.

In a further embodiment, a system for determining the thickness of a plurality of coating layers is provided, the system comprising:
  a sensor comprising pulsed source of THz radiation adapted to irradiate a sample comprising the plurality of layers with a pulse of THz radiation, the pulse comprising a plurality of frequencies in the range from 0.01 THz to 10 THz; and a detector for detecting the reflected radiation to produce a sample response derived from the reflected radiation,
  the system further comprising an analysis unit comprising a processor and a memory, the processor being adapted to:
  receive data describing the reflected radiation and sample response;
  access calibration data from the memory, the calibration data comprising initial values and search limits of optical parameters of the plurality of coating layers,
  produce a synthesized waveform using the optical parameters and predetermined initial thicknesses of the layers; and
  vary the thicknesses and vary the optical parameters within the search limits to minimize the error measured between the sample response and the synthesized waveform; and
  output the thicknesses of the layers.

The system may also be configured to calculate the calibration data from measurements of calibration samples, here, the system is further adapted to produce the calibration data, wherein the processor is adapted to receive first calibration data and second calibration data, the first calibration data comprising reflected THz waveforms from a first set of calibration samples and the second set of calibration data comprising reflected THz waveforms from a second set of calibration samples, the first set of calibration samples are samples with a substrate and a single coating layer and the second set of calibration samples have a substrate and a plurality of coating layers, the processor being adapted to select preferred refractive index models from data from a first set of calibration samples and determining initial values and search limits of optical parameters from data from a second set of calibration samples.

In a further embodiment, a sensor for a THz measurement system is provided, the sensor comprising:
  a pulsed source of THz radiation adapted to irradiate a sample with a pulse of THz radiation, the pulse comprising a plurality of frequencies in the range from 0.01 THz to 10 THz;
  a detector for detecting reflected radiation from the sample; and
  a movable mirror, said mirror being movable into and out of the path of the THz radiation at a position before the THz radiation reaches its focus,
  the sensor being configured to guide radiation reflected by the movable mirror back to the detector to provide an internal reference signal indicating the instrument response.

In an embodiment, the above sensor may further comprise a processor and memory, the processor being adapted retrieve from the memory a scaling function which relates the said internal reference signal to an external reference signal, the external reference signal being the signal measured when a mirror is provided at the focus of the THz radiation, said processor being adapted to reproduce an external reference signal from the internal reference signal and the scaling function.

In a further embodiment, a sensor for a THz measurement system is provided, the sensor comprising:
  a pulsed source of THz radiation adapted to irradiate a sample with a pulse of THz radiation, the pulse comprising a plurality of frequencies in the range from 0.01 THz to 10 THz;
  a detector for detecting reflected radiation from the sample;
  a non-THz measurement gauge adapted to measure the position from the sensor to the sample; and
  an indicator adapted to indicate when the measurement gauge indicates that the sensor is at a suitable distance for the sensor to make a THz measurement.

For example, the non-THz measurement gauge is selected from an ultrasound or laser gauge.

In a yet further embodiment, a sensor for a THz measurement system is provided, the sensor comprising:
  a pulsed source of THz radiation adapted to irradiate a sample with a pulse of THz radiation, said pulse comprising a plurality of frequencies in the range from 0.01 THz to 10 THz;
  a detector for detecting reflected radiation from the sample;
  an alignment laser, configured to show a single reflection on the sample when the sensor is angularly aligned to allow detection of the reflected THz radiation and to show multiple or distorted reflections when the angular alignment of the sensor is not correct. The above embodiments allow the problem of determining best-fit parameters values to synthesize a THz waveform to be simplified if the dimension and size of the solution space to be explored (by least squares minimisation) can be reduced, by applying constraints (and/or upper and lower bounds) on the possible values for the unknown quantities (thickness and refractive index). The problem of calculating individual coating thickness is greatly reduced if the optical response (refractive index) of all coatings and substrate are known in advance. Thus, given the optical properties (defined by initial values and upper/lower bounds on refractive index model parameters that may produce a constrained, but not necessarily fixed, refractive index) of each coating and the measured reflected signal, the thickness of individual coating layers can be calculated using a local optimisation routine to minimize the difference between the measured and simulated signals.

This allows reduced processing time with an accurate result that can be output for each layer and which can cope with variations in temperature and other conditions, present when the coatings were deposited, that, if not accounted for, would otherwise cause variations in the underlying parameters and models used to predict the thickness of the layers.

FIG. 1 shows a very basic overview of a system in accordance with an embodiment of the present invention. The system comprises a sensor 1 that will be described in more detail with reference to FIG. 2. In this embodiment, the sensor is a handheld sensor which will be guided over the coated body of a vehicle 3 by a user (not shown). In further embodiments that will be explained with reference to FIG. 12, the sensor is moved via computer control. The sensor is connected to analysis unit 5.

Figure 2:
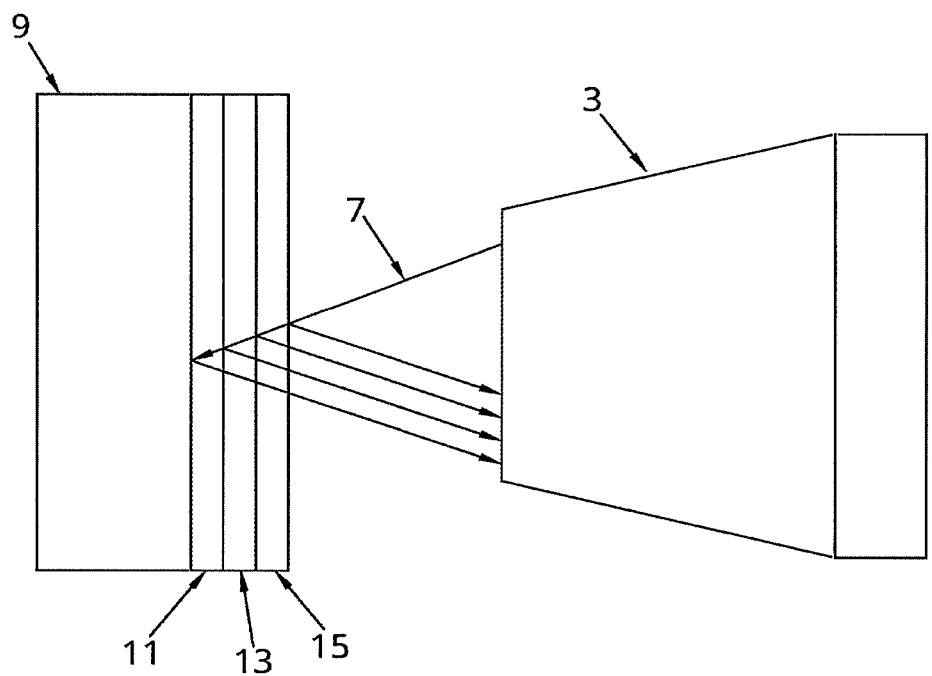
FIG. 2 is a schematic of a sensor performing a terahertz measurement and a coated sample.

FIG. 2 shows a simplified arrangement of the measurement that is made. The sensor 3 emits a broadband pulse of terahertz radiation 7 towards a panel 9 on the vehicle. The panel is a painted panel which has paint layers 11, 13 and 15. The terahertz radiation pulse will comprise a plurality of frequencies of radiation in the range from 0.06 THz to 4 THz. In this embodiment, three layers will be discussed. However, the method can be applied to any number of layers, from 2 upwards. Systems with 5 of more layers may be analyzed.

Each layer has a boundary with the previous layer and this boundary will cause a partial reflection of some of the terahertz radiation. The terahertz signal reflected from each boundary will have experienced a slightly different optical path (due to the thickness and optical response of the layer through which it passed) and therefore it is possible to determine the thickness of the layers accurately by the reflected terahertz signal.

However, the wavelength of the terahertz radiation is generally longer than the thickness of the layers. This makes the analysis of the signal difficult as it is not possible to simply identify the reflection from the surface of each layer. Furthermore, while FIG. 2 indicates the primary reflections from the four coating-coating and coating-substrate interfaces, the reflected terahertz radiation will also contain secondary and higher reflections from each interface, which will overlap with the primary reflections making straightforward analysis of the measured signal more difficult.

Figure 3A:
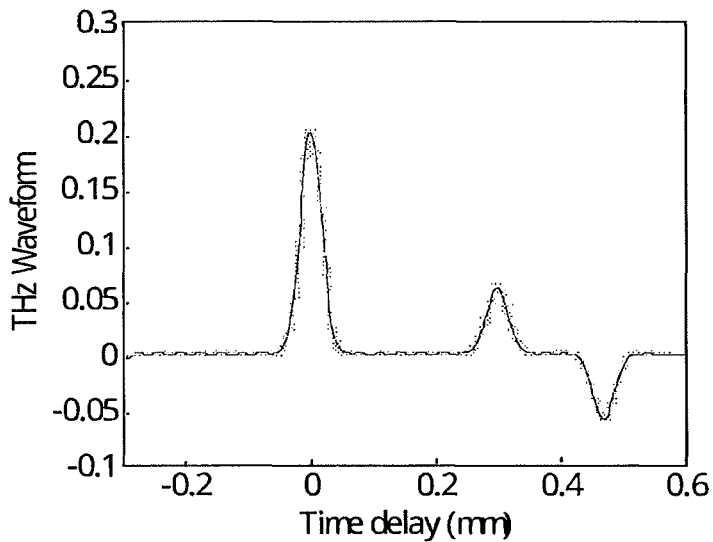
FIGS. 3(a) to 3(c) shows a trace of the time-domain waveform reflected from non-metal substrate with two coatings of different refractive index ($n_2 > n_1$)
Figure 3B:
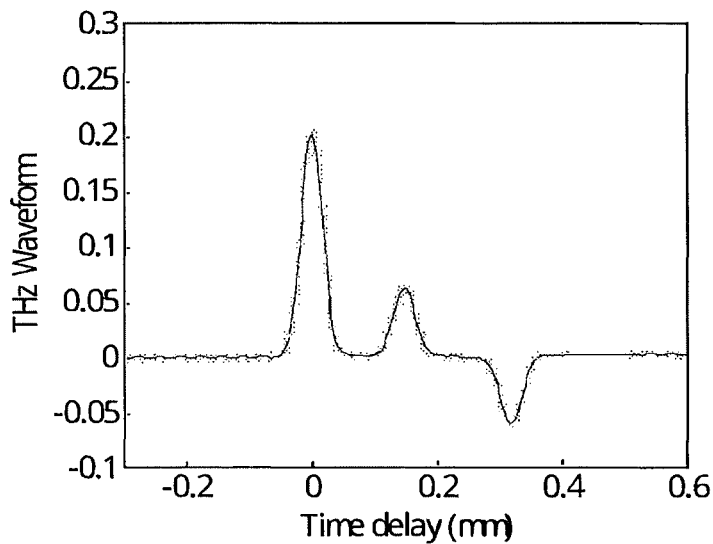
Figure 3C:
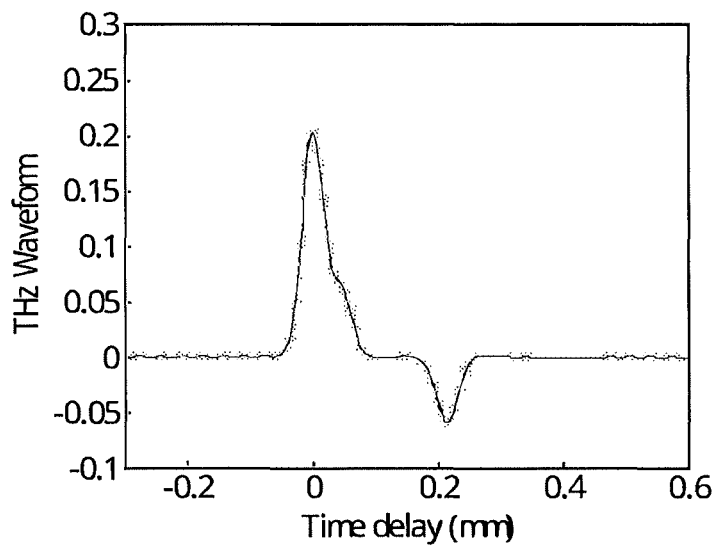

FIGS. 3(a) to 3(c) shows a trace of the time-domain waveform reflected from non-metal substrate with two coatings of different refractive index ($n_2 > n_1$). In FIG. 3(a), the large thickness of coating 1 means reflection peak 1 (from air-surface interface) and reflection peak 2 (from interface between coatings 1 and 2) are easily distinguished. In FIG. 3(b) the reduced thickness of coating 1 results in a decreased separation between reflection peaks 1 and 2. Finally, in FIG. 3(c), reflection peaks 1 and 2 can no longer be seen due to thin coating 1.

Figure 4:
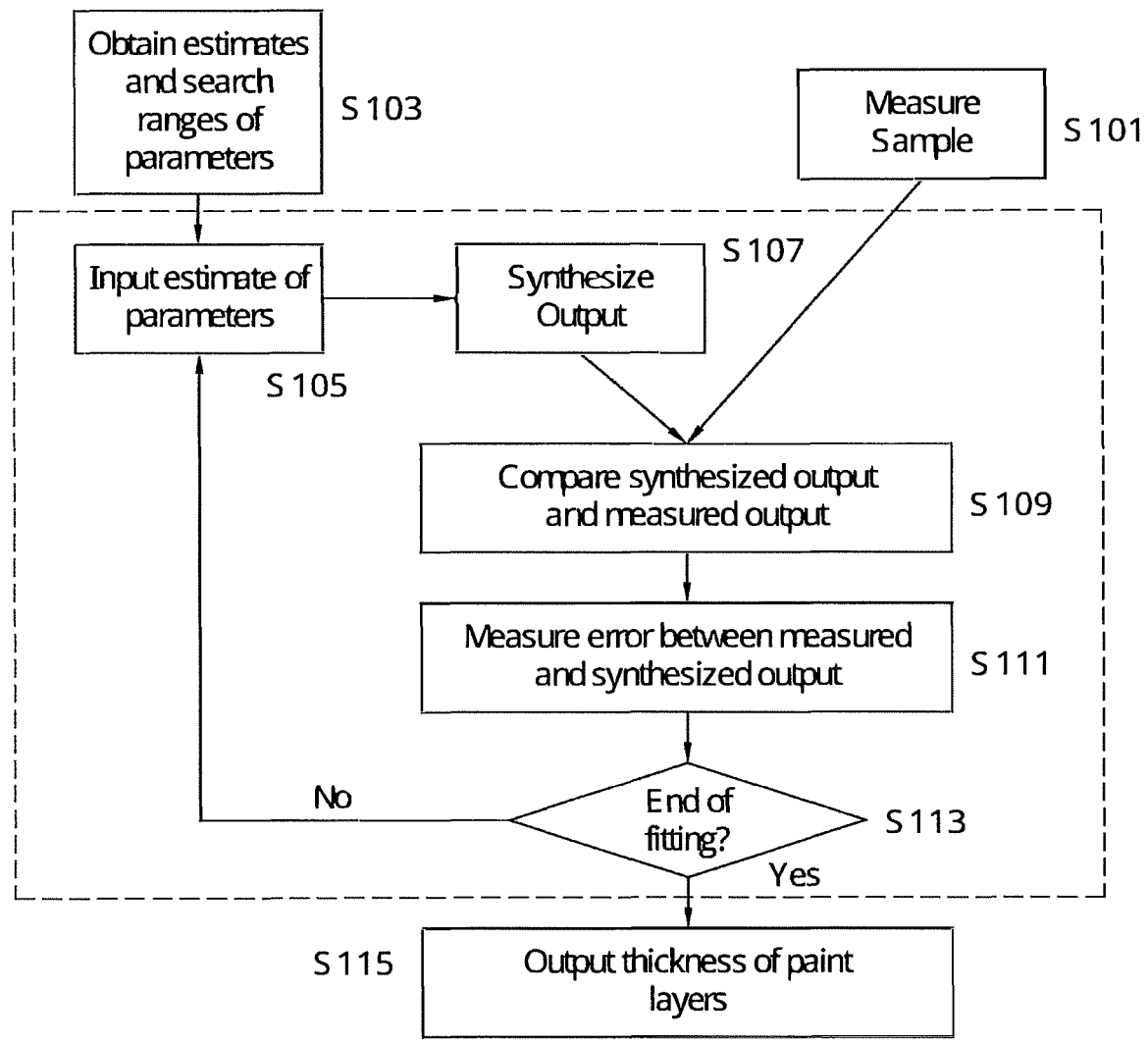
FIG. 4 is a flow diagram illustrating a basic method in accordance with an embodiment of the invention.

FIG. 4 shows a flowchart of the basic process which is used for determining the thickness of the paint layers. While it is possible to represent the optical properties of the individual coating layers by highly complex refractive index profiles that are parameterised by a large number of variables in order for a minimisation routine to produce a solution that approaches, or indeed achieves, zero difference between synthesized and measured signals, the fact that the measured terahertz response from the coated sample cannot support such a large number of variables corresponds to a system that is over parameterised. Such a solution might not physically represent the true response from the measured sample, thus leading to inaccuracies in best-fit parameters.

For the same reason, the large number of variables relative to the information content of the measured signal will mean that each parameter will have a large associated uncertainty, thus reducing the precision that could be attributed to best-fit values of coating thickness. Finally, an overly complex representation of the measured system, as described by a large number of free parameters, corresponds to a high dimensional solution space that will require increased time to converge to a solution. The algorithm described with reference to FIG. 4 at least partially addresses these issues by representing the measured system with the minimum level of complexity needed to describe reflection from the multi-layered system in a way that can accurately reproduce the thickness of the individual coating layers present.

In step S101, the method first determines the preferred optical models for the individual layers present in a given multi-layered coated substrate, as well as the extent of and starting point within the multivariate solution space, i.e. initial estimates of and bounds on individual model parameters. Possible examples of how the models and their constituent parameter values may be estimated will be described with reference to FIGS. 7 to 9. The parameters will be estimated with a range of possible values and not just a single value. Once these ranges have been estimated, the algorithm will seek to derive thicknesses using parameters within these ranges.

In an embodiment, the parameters fall into 2 basic groups, the first group represent the thickness of the layers, the second group are the optical parameters that define the response of the layers. Examples of the optical parameters can be the complex refractive index, complex absorption coefficient etc. The optical parameters define the complex-valued frequency-dependent refractive index profile and therefore provide for absorption and or scattering losses imparted on the terahertz signal by each coating material.

Figure 5:
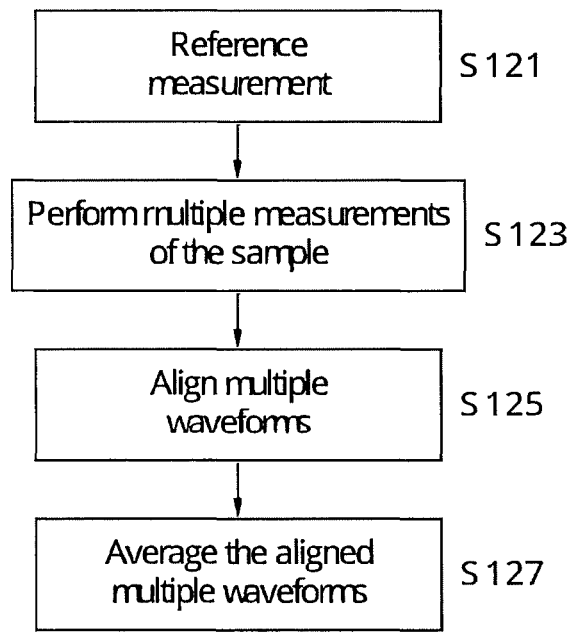
FIG. 5 is a flow diagram of the measurement steps performed on a sample.

In step S101 the sample is measured. The measurement of the sample will be described in more detail with reference to the flowchart of FIG. 5.

Next, the parameters to be first tried will be selected in step S105. In an embodiment, these will be the output of the calibration process which takes place in step S103. Then, the output from the algorithm will be synthesized in step S107. The sample will be measured in step S107. The measurement of the sample will be described in more detail with reference to the flowchart of FIG. 5.

In step S109, the synthesized output from step S107 is compared with the measured sample output from step S101. The error between the synthesized output and the measured output is then determined in step S111. It is then determined in step S113 if the fitting has finished. The end of fitting can be determined in a number of different ways. For example, the number of iterations may be a fixed number. In other embodiments, a check is made to see if the error is the minimum error. In further embodiments, other stopping criteria are used to check whether the optimisation routine has converged on a local solution. If at step S113 it is determined that the end of the fitting has not been reached, then the set of parameters are updated and a new output is synthesized in step S105. Then the process starts again. Once a solution has been determined, the system outputs the thickness of the paint layers in step S115.

The dotted line in FIG. 4 represents the steps that are looped though to arrive at the solution via iteration.

The specifics of the above steps described briefly in FIG. 4 will now be explained. FIG. explains how the sample is measured in accordance with an embodiment of the invention. In its simplest form, the measurement is performed by irradiating the painted car panel with a pulse of THz radiation and collecting the reflected signal.

The signal emitted (and received) by the terahertz sensor 3 (FIGS. 1 and 2) can vary over time due to changes in both the environment (temperature and humidity) through which the emitted and reflected terahertz beams propagate and in the terahertz instrumentation itself. Such changes in the system response must be accounted for when extracting the sample response which can be done by ensuring that whenever a sample measurement is taken, a corresponding reference measurement is also acquired. In an embodiment, all point measurements therefore consist of the acquisition of two reflected terahertz time domain waveforms: a reference waveform and a sample waveform. The reference waveform describes the instrument response at the time the measurement was made and is removed from the sample waveform to reveal the response due to the presence of the measured sample only, independent of the particular instrument used to perform measurements.

Figure 6A:
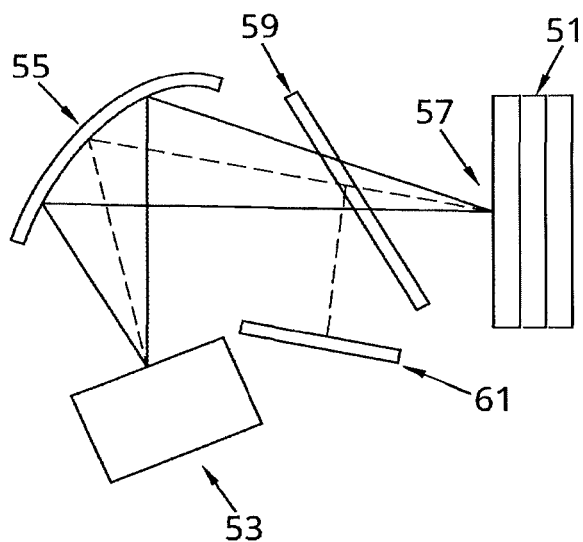
FIG. 6(a) is a schematic of the sensor head and radiation parts for both actual measurement and a reference measurement.

FIG. 6(a) shows the internal configuration of terahertz sensor measuring a sample 51. The sample comprises a plurality of layers and is provided at the focus of the terahertz sensor. The terahertz sensor comprises a unit 53 which both emits and detects terahertz radiation. The radiation when leaving the terahertz unit is brought to focus by an optical element (e.g. a mirror) 55 at the focal plane 57 in the vicinity of the sample 51. In a separate reference measurement, a plane mirror (not shown) is provided at the focus 57 to allow the terahertz beam to be reflected back from the focus to the detector in unit 53.

However, as explained above, in an embodiment, reference measurement is performed before every sample measurement. This can be achieved without a mirror at focus 57 by the provision of movable mirror 59. Movable mirror 59 is provided so that it can move into the field of the terahertz beams or move out of the field of the terahertz beams as required. When movable mirror 59 is provided in the field of the terahertz beams, the emitted beam is redirected towards a further plane mirror 61. The reflected beam then reflects back towards movable mirror 59, back towards curved mirror 55 and then into unit 53.

The provision of this movable mirror 59 therefore allows a measurement of the instrument response to be performed without the need to place a mirror at focus 57. However, the optical path of the terahertz radiation to the movable mirror and back to the unit 53 is slightly different to that from the unit 53 to the focus 57. However, a calibration measurement can be performed which provides a scaling factor which allows the reference measurement made using the plane mirror 61, via movable mirror 59, to be modified to be the same as if the reflection came from a plane mirror at the focus 57.

The optical configuration of the sensor 3 consists of two separate terahertz beam paths that are fed by same emitter and detector devices: a sample 51 is placed at the focus 57 of the terahertz beam along the external path and a plane mirror 61 (to record the system response) is fixed in position at the focus of the terahertz beam along the internal path.

By providing two separate terahertz paths, that can be selected using intersecting plane mirrors 59, a reference can be acquired from the internal beam path for every sample measurement that is made on the external beam path without the need to disturb the sample by replacing it with a plane mirror. However, because the two optical beam paths are not identical the reference acquired from the internal beam path represents a system response that does not match exactly the system response that would be measured from the external beam path.

By recording the system response (reflections from identical, correctly aligned, in-focus plane mirrors) at the end of both paths, a complex-valued frequency-dependent scaling factor H(v) that relates the system response from one path to the other can be derived as follows $$H(v) = R_{external}(v) / R_{internal}(v)$$

where the frequency-domain representation R(v) is given by the Fourier transform via fast Fourier transform (FFT) of the measured time-domain reference waveform r(t) as $$R(v) = FFT\{r(t)\}$$

This reference scaling factor H(v) is stored on the system and for all subsequent measurements is used to create an external system response by scaling the measured internal system response as:

$$R_{external}(v) = H(v) \cdot R_{internal}(v)$$

For the handheld variant of the sensor, a dedicated sensor mount containing an external mirror fixed at the external focus 57 is utilised. For a robotically positioned sensor, the external mirror would be fixed in position known to the robot inside the robotic inspection cell. Reference calibration acquisition is performed as the last step in system installation (after system has stabilised to surrounding environment) and may be required upon changes of relevant hardware components of the terahertz measurement system.

Figure 6B:
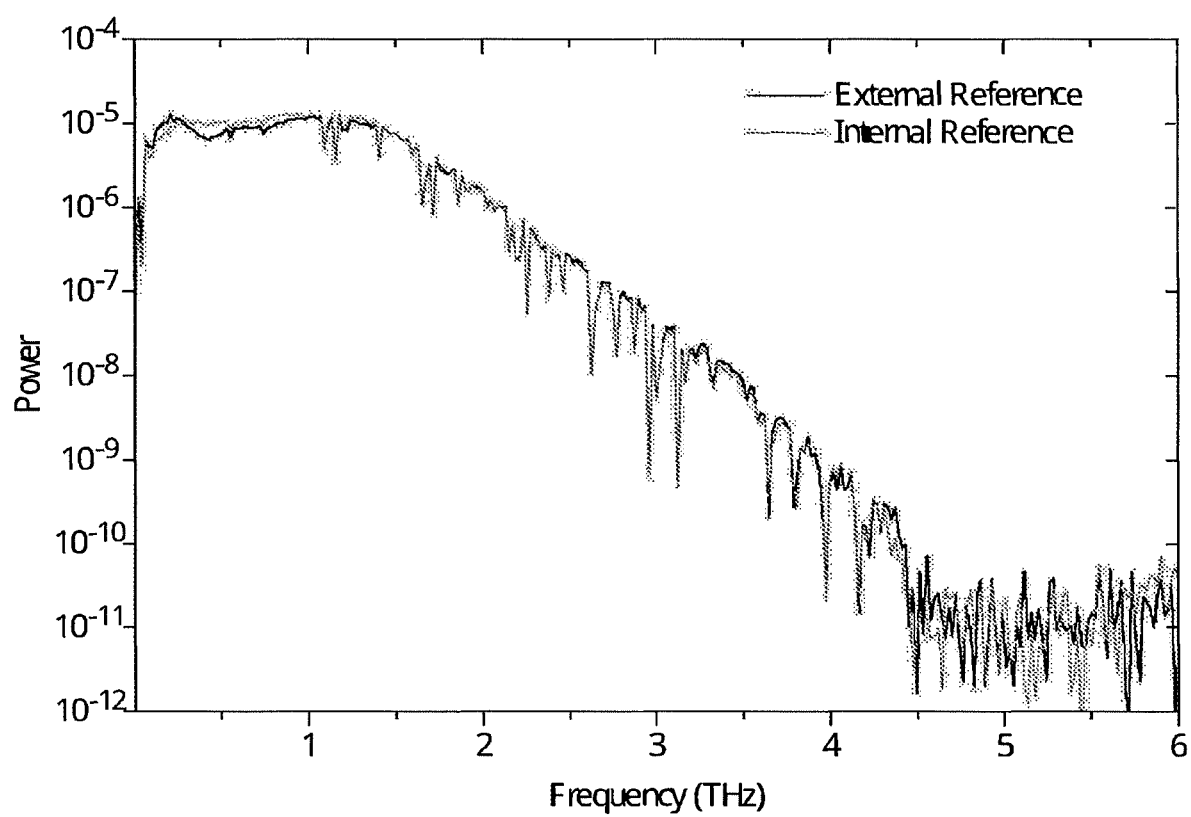
FIG. 6(b) is a frequency domain waveform showing how an internal reference can be scaled to produce the output of an external reference.

FIG. 6(b) shows the FFT of both the internal and external reference signals. It can be seen that deviations occur at high and low frequencies. The purpose of the reference calibration is, as far as possible, to 'map' the internal reference measurement onto the external reference measurement.

As mentioned above, two independent measurements of the reflected terahertz signal (time-domain waveform) are performed: a reference measurement from the internal reference mirror 61 and a sample measurement from the surface of a sample (coated substrate) placed at the focus 57 of the external terahertz beam path.

To increase quality of the measured signal, each measurement consists of the co-average of multiple individual waveforms, the number of which is dependent on signal quality and desired signal integration time in step S123.

Next, as indicated in step S125, the individual waveforms are co-aligned such that the strongest reflection in each individual waveform occurs at the same time delay. Then in step S127, the aligned waveforms are averaged. If alignment is not performed, the co-averaged signal will not be representative of any individual waveform but will instead contain a corrupted version of the information contained in the signal reflected from the measured sample.

In the standard mode of operation, this is used for collection of data for thickness measurements at one or more locations on a coated substrate. Thickness of coating layer(s) can be calculated either immediately after each measurement is complete, or deferred until such time as a, possibly pre-defined, set of measurements has been collected. Calculation deferral avoids delays between sequential measurements so as to allow multiple measurements (e.g. a measurement job for a particular vehicle body type may consist of measurements at ~100 pre-defined locations on the vehicle) to be completed in the shortest time possible thereby increasing throughput in terms of the number of vehicles that can be processed in the inspection bay per shift. Point thickness measurement can only be performed when a calibration has been selected (either manually by an operator, or automatically by reading the alphanumeric code of the paint colour that has been applied to the vehicle presented for inspection).

In an embodiment, guidance is provided to ensure that the sensor is correctly positioned. In one embodiment a gauge, e.g. a laser gauge is provided to determine if the sensor is in the correct position to perform a measurement. When the sensor is hand held, the laser gauge may be configured to indicate to the user the correct position, e.g. show a red light when the sensor is in the incorrect place and a green light when the sensor is in the correct place.

A robotic system may have automated sensor positioning. Positioning the sensor such that the measured surface is at focus and normal to the direction of the terahertz beam is done by adjusting the sensor position and orientation until properties of the terahertz signal reflected from the surface (signal amplitude and offset between surface and terahertz focus) indicates that ideal orientation and position has been achieved.

In all cases where it is necessary to compare a synthesized waveform with that of an actual measurement regardless of whether this is for calibration measurements or actual measurement, it is important to remove the response from the instrument to isolate the sample response. It is also necessary to ensure that any offset due to the position of the sample and any tilt in the sample is also corrected for.

The response from the instrument can be removed by deconvolving the response from the sample with that from the instrument. The response from the instrument is measured as described above.

Variations in the position of the sample surface relative to the focus of the sensor introduces a linear phase shift in the measured frequency domain sample response that can be accounted for by first determining the distance between the coated surface and the terahertz focus. At first, this appears quite an easy problem until it is considered that the reflection from the top surface of the sample may not be the strongest reflection. For example, for a sample in which the coatings have been applied to a metal substrate, the strongest reflection will typically be from the substrate itself rather than from any of the preceding layers.

In an embodiment, this problem is addressed by identifying the location of the surface reflection peak in both the simulated and measured waveforms and assigning the difference in these positions as an estimate of the offset between measured surface location and terahertz focus. Necessarily, the simulated waveform is generated such that the simulated coating structure is at focus. In the case where the top most coating layer has a sufficiently large thickness that, after deconvolution with the reference waveform, the reflection peak from the air-to-surface interface can be clearly distinguished from the next reflection peak (from the subsequent coating-to-coating or coating-to-substrate interface), the simulated and measured surface reflection peaks locations are identified by analyzing properties (location, width and height) of the surface reflection peak that is first identified by thresholding the deconvolved measured waveform above the full-width at half maximum signal amplitude contained in the simulated waveform. For a top-most coating with a thickness that is too thin for the individual reflection peaks from the surface and next interface to be clearly distinguished, the location of the surface reflection peak cannot be directly determined through analysis of the deconvolved waveform. Instead the raw measured waveform is examined to identify the location of the strongest pre-pulse feature of the raw reference waveform the presence of which in the measured sample waveform indicates the location in the measured waveform where reflections from the measured sample surface are contained. For a given measurement, the first method is attempted and if unsuccessful (because the first and second reflections cannot be clearly distinguished), the second method is used instead.

In a further embodiment, the tilt of the sample is also corrected. Ideally the sensor is operated with the coated surface in focus and oriented such that the coated surface is normal to the terahertz beam path. Away from normal orientation, the amplitude of the waveform reflected from a plane surface will decrease by the same factor across all frequencies, thus any reduction in measured signal strength due to non-normal operation can be represented in waveform simulation by multiplication of simulated waveform by a constant scaling factor that decreases with increasing angle from normal incidence and is at a maximum at normal orientation. For analysis (calibration or layer thickness calculation) of measured waveforms made when the coated surface is known to have been at normal orientation, this scaling factor can be omitted (by fixing at unity) thereby reducing the complexity of the numerical simulation to be optimised. In the case of calibration this reduces the number of parameters to be optimised, which in turn allows the remaining parameters to be determined to a greater degree of accuracy and lower uncertainty.

Systems in accordance with embodiments of the present invention are designed to provide initial estimates and confidence limits for those estimates. The systems are also configured to measure the sensor response to ensure that this is removed from the sample response. Further, measurements are performed to allow the synthesized waveform to accurately match the measured waveform.

In one embodiment, two sets of calibration measurements are performed. Before coating thickness can be calculated, a description of the optical response from the individual coating and substrate materials is required. A number of factors (including film formation and the fact that coatings can be sub-wavelength) means that material characterisation is best performed, not on measurements of each coating material in isolation, but rather on measurements from samples of the same coating-substrate structure, for which coating thickness will subsequently be calculated. As when calculating individual coating thickness, least squares fitting is used to generate a candidate calibration (that describes the refractive index of each coating layer and non-metal substrate). The particular form factor used to describe the profile of the frequency dependent, complex-valued refractive index is determined by characterising the coating material from measurements of the coating material that has been applied to a metal substrate only. A number of optical models are trialed and the optimum automatically determined.

The first of these measurements is performed on single-layer samples. The single-layer samples are used to estimate the optical properties of the layers to be measured. The second of these measurements is then used to refine those optical properties for the same coating materials but that are now presented as a combined stack of coating layers. The validity of the refined optical properties is verified by ensuring that when used for thickness calculation they will produce a set of coating thicknesses that match, within a known level of uncertainty, the expected thickness of the plurality of layers provided on the calibration sample(s), as measured by independent means (e.g. by optical microscopy).

Figure 7A:
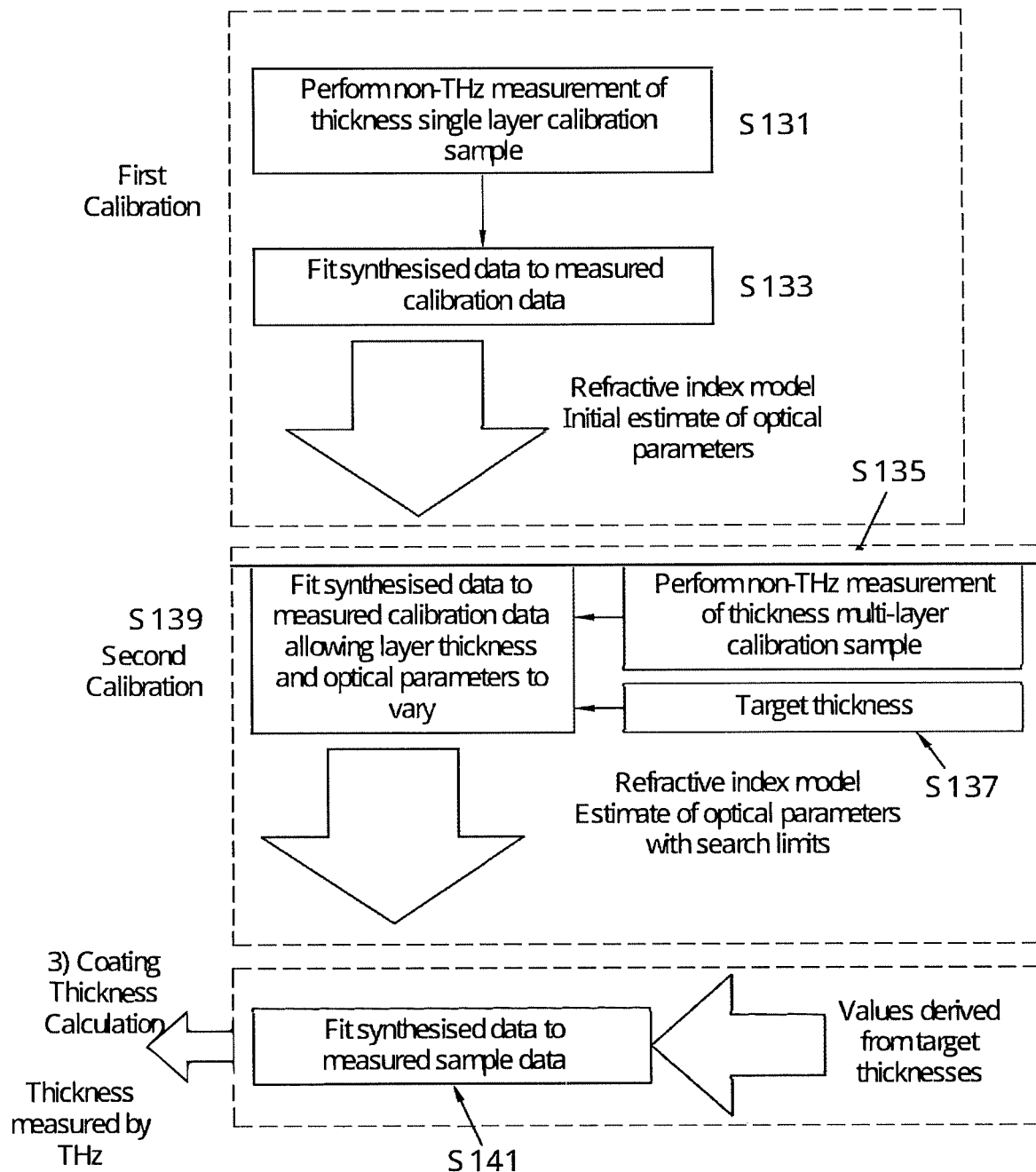
FIG. 7(a) is a flow diagram showing how the calibration steps prepare data for the fitting of the data for the sample.
Figure 8A:
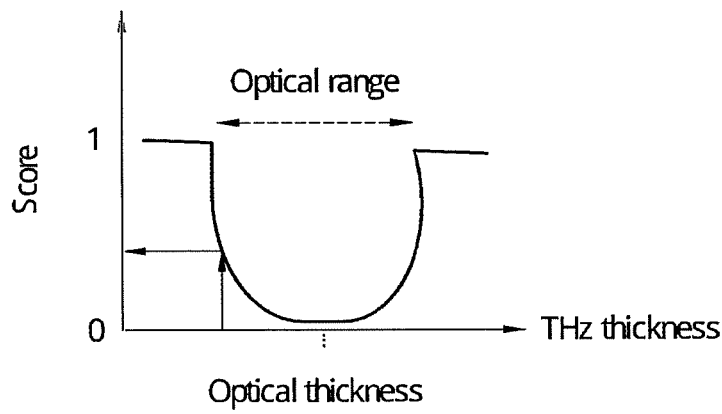
FIGS. 8(a) to 8(c) are figures showing how an optical model is selected.
Figure 8B:
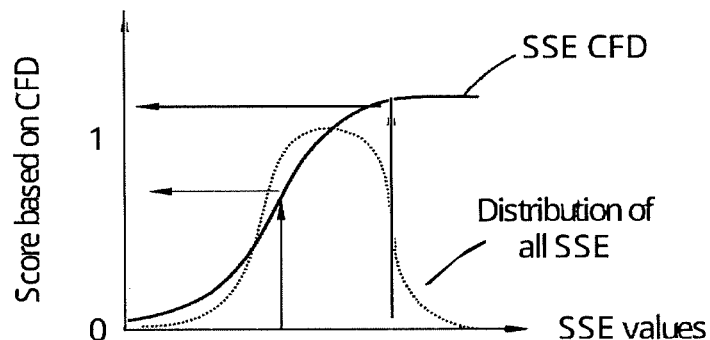

FIG. 7(a) is a flow chart showing how parameters derived from a first and second calibration are used in the fitting of the data from the sample.

In step S131, non-THz measurements are performed to determine the thickness of the layers of the single layer samples. In an embodiment, single-layer coating samples are provided on metal substrate. For thickness calculation of coating(s) on a non-metal substrate, a separate uncoated substrate will be supplied from which its optical properties can be estimated in the absence of any coatings. If the non-metal substrate is thin enough to allow a terahertz measurement to capture reflections from the front and back of the substrate in a single measured waveform, the thickness of the substrate will be used as input to estimate its optical properties, by treating the thin substrate as a layer on a substrate of air. For a thick non-metal substrate, the substrate will be treated as an uncoated substrate whereby its optical properties must be estimated by assuming it is of infinite thickness.

At least one single calibration layer sample will be provided for each layer of the sample to be analyzed. The thickness can be measured using an optical microscope, ultrasound etc. The data is then fitted to determine a refractive index model and an initial estimate of the optical parameters in step S133.

The refractive index model and the parameters are then fed into the second calibration synthesis step S139. Along with the optical parameters and model, measurements of the thicknesses S135 of the second calibration sample and target thicknesses S137 are provided to the fitting step. The target thicknesses are the thicknesses that the layers are intended to be. However, it should be noted that during step S139, the layer thicknesses are allowed to vary as its assumed that there may be an error in these calibration measurements of the thicknesses. The output of this step is the refractive index models to use and estimates of optical parameters with the search limits.

Finally in step S141 the output of step S139 is provided to the fitting model with the values of the target thickness of the layers. The output of the layer thickness is accompanied with confidence scores on these limits, these are derived from the accuracy of the fit of the model to the data.

To aid readability, the two calibrations stages and the analysis of the sample are shown as three separate stages in boxes with dotted lines.

Figure 7B:
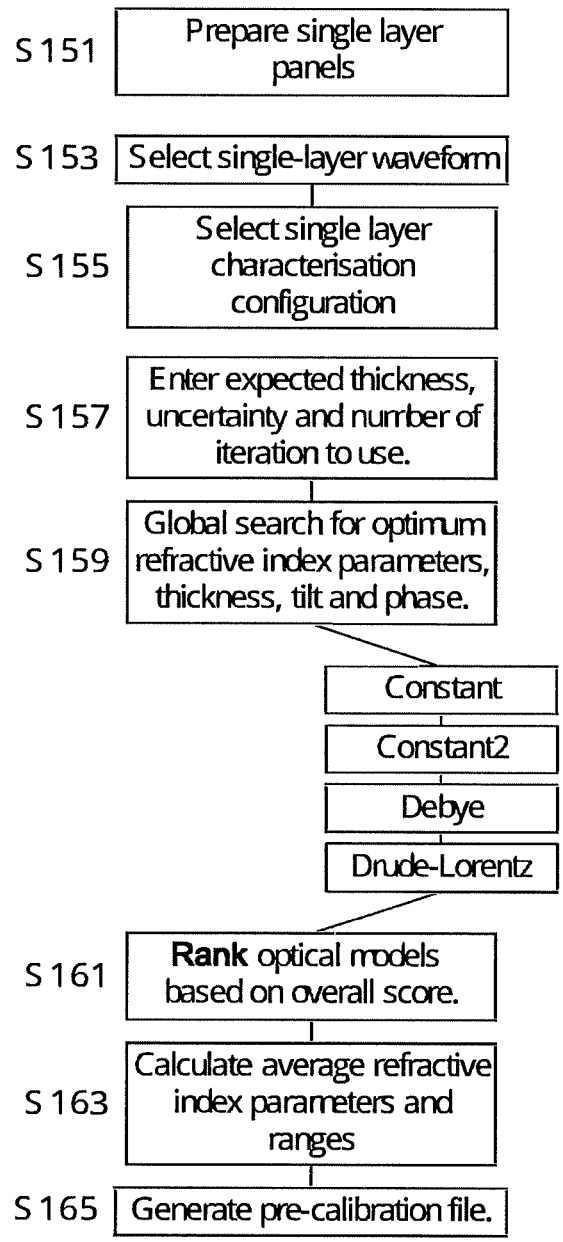
FIG. 7(b) is a flow diagram showing the basic steps performed during calibration using a single layer calibration sample.

FIG. 7(b) is a flowchart showing the process for measuring a single layer and the calibration steps taken.

In step S151, single-layer panels are prepared. To minimize the number of variables involved the coated samples used for calibration should consist of one or more coatings applied to a flat substrate, rather than one with curvature. In the case of single-layer panels, the coating should be applied at a suitably high thickness so that the optical response to that coating material can be determined unambiguously. The coating thickness required for single-layer calibration will vary by coating type but typically the coating should be applied at a thickness of at least 25-30 µm, or the target coating thickness, whichever is greater (e.g. Clearcoat and powder primers are typically applied at thicknesses in excess of 50 µm). For highly metallic coatings (those with a high loading of aluminium flake) a lower film thickness should suffice. The other requirement for preparation of single-layer panels is that the coating is applied to an uncoated aluminium substrate to ensure only the coating of interest is contained on a substrate that will be less prone to corrosion (during transport, storage, etc. between the time of preparation and measurement).

In step S153, the system is so that it is measuring a single layer waveform. This allows it to select a single layer characterisation configuration in step S155. In step S157, the expected thicknesses, uncertainty number of iterations to use are entered.

Next, the waveform for single-layer sample is synthesized and an iterative procedure is performed to determine the optimum refractive index parameters, thickness tilt and phase in step S159. Also in this step, the model which is most suitable for examining the optical response of the single-layer sample is deduced. This document indicates that the routine examines the use of four different refractive index models ('Constant', 'Constant2', 'Debye' and 'Drude-Lorentz') with which to describe reflection from the measured single-layer sample. After generating multiple sets of best-fit parameters for each refractive index model, via a global optimisation search routine (in this embodiment Differential Evolution), a ranking scheme (described in relation to FIG. 8) is applied to determine which of the refractive index models is best suited to describe the measurement.

In the described embodiment, the different models are of varying complexity: the simplest (Constant) is described by two independent parameters and the most complex (Drude-Lorentz) is parameterised in terms of at least 4 arguments.

These four refractive index models are purely used as an example and alternative models could be additionally or alternatively used. Additional refractive index models of greater complexity that are best suited to approximate the frequency-dependent, complex-valued refractive index of a given material could also be used. For example, the complexity of the Drude-Lorentz model could be increased by the addition of 3, 6, 9, etc. terms, that describe frequency-dependent features of the refractive index profile. Also less than four models can be used or more than four.

The greater the complexity of the refractive index model, the more accurately it may be able to represent the refractive index for a given material. However, it may also be possible to represent the refractive index of a given material with a less complex function, such as the 'Constant' model which assigns frequency-independent constant values to the real and imaginary parts of the refractive index. There is no advantage in representing the refractive index of a given material with a model that has complexity greater than that which is required to accurately reproduce through numerical simulation the measured terahertz signal reflected from a sample containing that material for the combination of known or expected layer thicknesses contained in that sample.

In fact, by increasing the level of complexity with which the refractive index of materials are represented, it is possible to reduce to (essentially) zero the difference between measured and simulated terahertz signals. However, the resulting simulation may correspond to individual layer thicknesses that do not represent the true thickness of the sample layer(s).

Figure 8C:
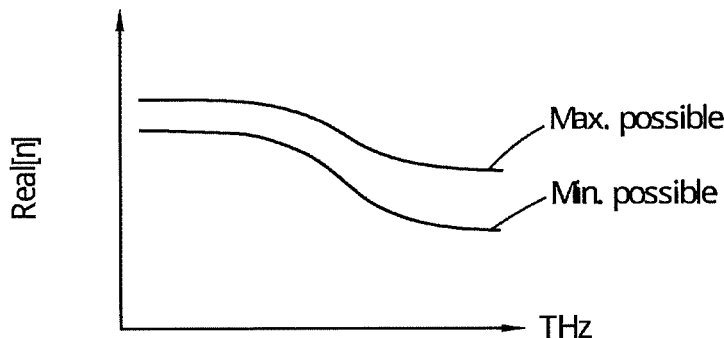

Therefore an objective of the calibration routine is to determine a numerical model that describes the refractive index profile for each material that will reproduce the measured terahertz signal reasonably well for a combination of layer thickness values that correspond to actual layer thickness values FIG. 8 shows how the different models can be ranked in order to automatically determine which model is best suited to represent the coating layer. These tests are applied to the sets of best-fit parameters produced by the multiple global optimisation routines that have been applied for each model. The result of each test are weighted and then combined to produce a score for each refractive index model and the model with the lowest score is selected as being the most suitable model for the particular coating layer.

For each model the four tests take into account:

Test 1) (FIG. 8a) how well the best-fit thickness matches the expected thickness of the single-layer panel Test 2) (FIG. 8b) the spread in sum of squared errors for the best-fit parameters Test 3) (not shown) the complexity of the refractive index model, as given by the number of parameters needed to describe the model Test 4) (FIG. 8) the spread in frequency-dependent refractive index values The tests are then combined to produce a score where lower scores are better. In an embodiment, the score is calculated as follows:

$$\text{score} = w1 f1(\ldots) + w2 f2(\ldots) + w3 f3(\ldots) + w4 f4(\ldots)$$

Suggested weights, w1=1000, strongly favour optical models that predict the optical thickness.

w2=100, favour optical models with low SSE w3=50, favour optical models with small number of parameters w4=10, favour optical models with small spread in possible refractive index values In step S163 the parameter values and ranges are defined. As said above, for each tested refractive index model global optimisation is applied multiple times (from different, randomly selected starting points). For each mode, the average of the best-fit parameter values from the multiple trials are assigned as the overall best-fit parameter values for that model, while the minimum and maximum best-fit parameter values are assigned as the upper and lower search ranges for subsequent use.

The output of the system is also the optical models ranked.

The multiple layer samples are then measured. It is desirable for the multiple layer samples to be prepared in the same way as the paint which is to be measured which is eventually applied to the vehicle. For example, if wet on wet coating is used, where the next coating is applied before the previous coating has had time to dry, then the calibration sample should be prepared in the same way. In one embodiment, the calibration samples are prepared on the car production line in exactly the same way as the vehicles which are to be coated. The multiple layer calibration samples are also provided on the same substrate as the coatings will appear on the vehicle.

In step S201, a separate measure is performed of the thickness of the layers, for example using optical microscopy et cetera. This data along with the calibration files which contain the ranked optical models derived as explained with reference to FIGS. 7 and 8 is then provided to the system in step S203.

Terahertz measurements are then performed at different locations on the calibration sample. A synthesized waveform using the above parameters is then fitted to the measured waveform the same way as described above. Here, corrections made for the phase in step S205, the tilt and thicknesses and the optical parameters. Fitting is then performed in the same way as described above.

If the optical thicknesses output are what is expected identity they fall within the confidence limits of the measurement from the other modality, then these thicknesses and their confidence limits are used for the next step. However, if they are not, there may be a problem with the underlying optical model which was previously selected. The optical model is modified and then the fitting process is repeated.

Once the calibration has been completed, it is possible to measure real samples using the optical models determined above, the optical parameters with the confidence limits and also the estimate of the thickness of the layers and their associated confidence limits.

The substrate should also be considered at the calibration stage.

The above system can cope with any substrate, for example: carbon fibre; ABS (acrylonitrile butadiene styrene); RIM (reaction injection moulding); polyurethane; SMC (sheet moulded composite); glass-fibre reinforced polyester; or carbon fibre reinforced plastic (CFRP).

The above system, can cope with both 'thin' substrates (where the pulse returned from the rear substrate-air interface is visible) and also the 'thick' substrate (where the pulse returned from the rear substrate-air interface is not visible).

Identifying the contribution from the substrate to a measured signal reflected from a coated substrate is difficult for a number of reasons, including:

1) For thin coatings on metal substrate, the reflection from the substrate may not be easily identifiable due to the overlapping of reflections from neighbouring layer interfaces 2) For non-metal substrates, the difference in refractive index between substrate and the coating on top may be small thus reducing the reflection from the substrate which, as above, will makes its position difficult to identify with any certainty.

The presence of coating(s) that have different thicknesses, refractive index and absorption profiles on a substrate mean that the position, amplitude and shape of the reflection from a coated substrate can vary significantly, not only between samples having different coating combinations but also between samples with the same coating combination but different individual layer thicknesses.

In one method, the substrate is treated as one of the layers during the multilayer calibration.

In an alternative method, the substrate has an independently characterised refractive index and this is used in the model when determining the thickness of the layers.

For polarisation sensitive substrate materials (e.g. CFRP) that infer a preferred direction about the z-axis at which reflection measurements should be made can include sensor rotation about its z-axis to maximise reflected signal.

Metal substrates can be treated as ideal reflectors. The terahertz signal doesn't transmit through metal therefore there will not be a reflection from the back of a metal substrate. Therefore, there is no need to calibrate for the metal substrate. Calibration in the presence of non-metal substrates is possible on substrate in isolation for a thin layer of substrate in air; otherwise calibration done in-situ as part of multi-layer calibration Next with reference to FIGS. 9(b) to 9(i) a calibration routine and an enhanced calibration routine will be discussed.

Figure 9A:
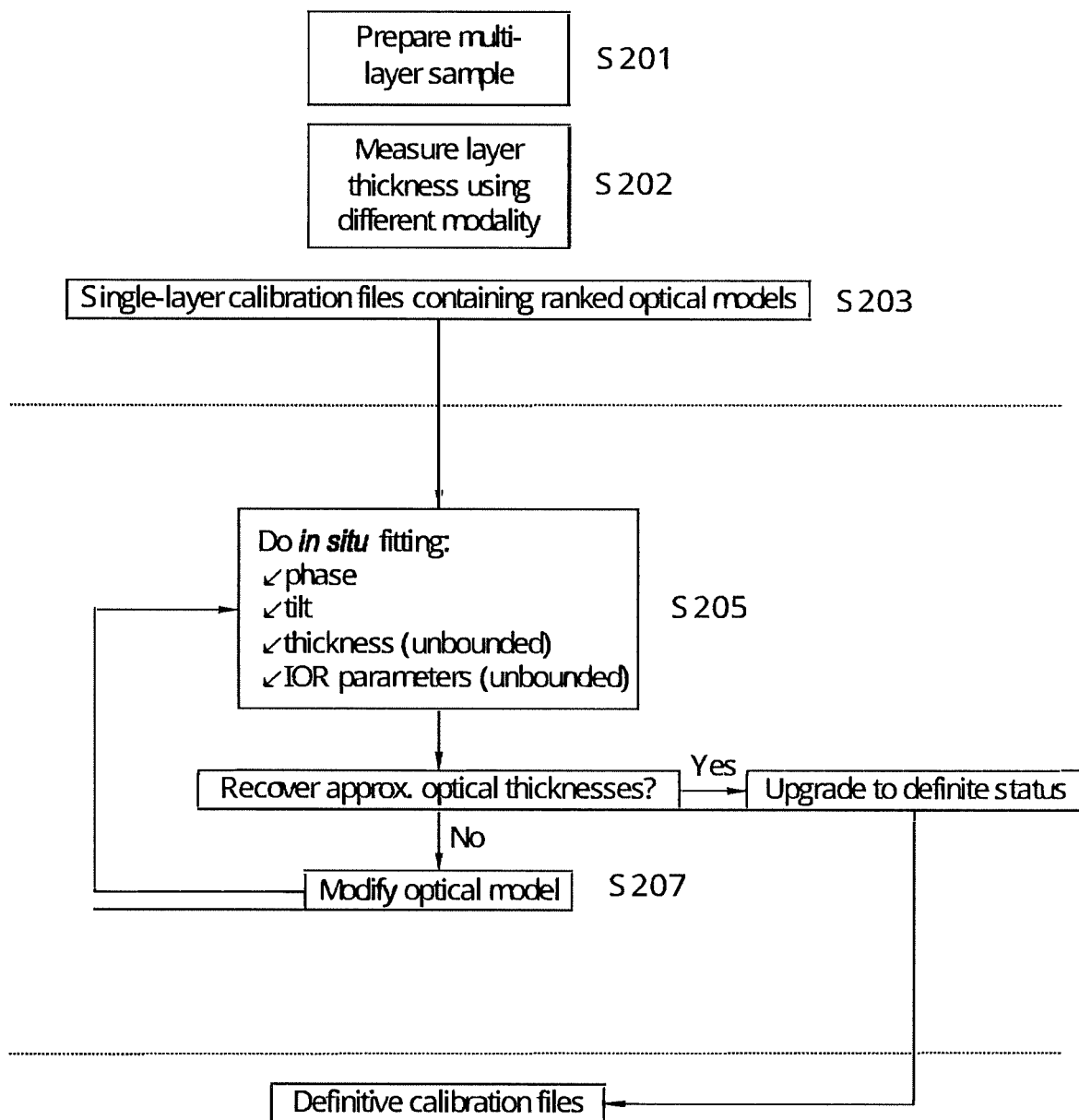
FIG. 9(a) is a flow diagram showing the basic steps performed during calibration using a multilayer calibration sample.

FIG. 9(b) is a panel defining the datasets that will be used in the following flow diagrams. FIG. 9(c) is a panel showing the algorithmic operators that will be used in the following flow charts. FIG. 9(d) is a panel detailing the operations performed in the calibration steps.

It should be noted that expected and predicted thickness combinations T and P include information relating to the level of uncertainty associated with thickness values.

Figure 9E:
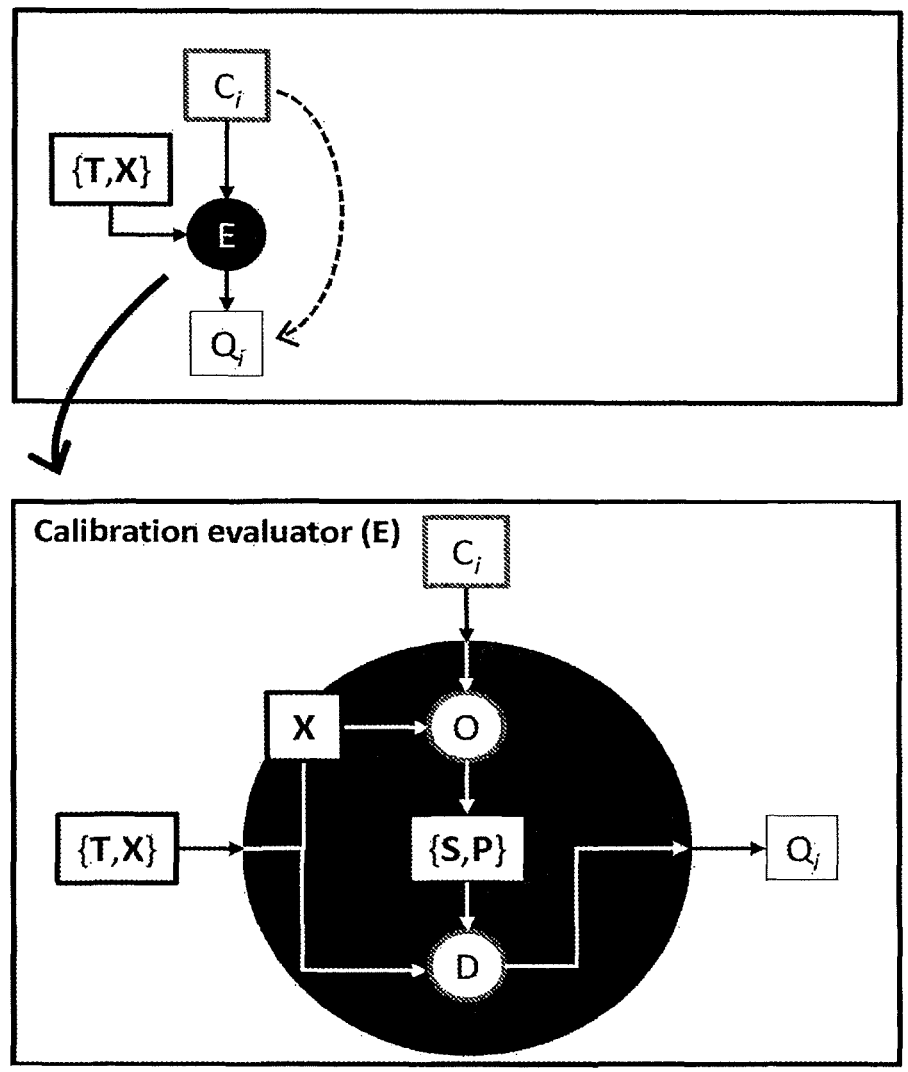
FIGS. 9(e) and 9(f) illustrate the concepts of evaluating the quality of a given calibration as well as the relationship between single-layer calibrations and a multi-layer calibration.
Figure 9F:
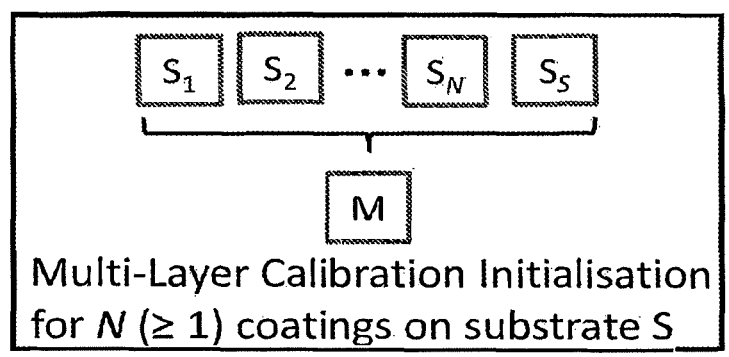
Figure 9G:
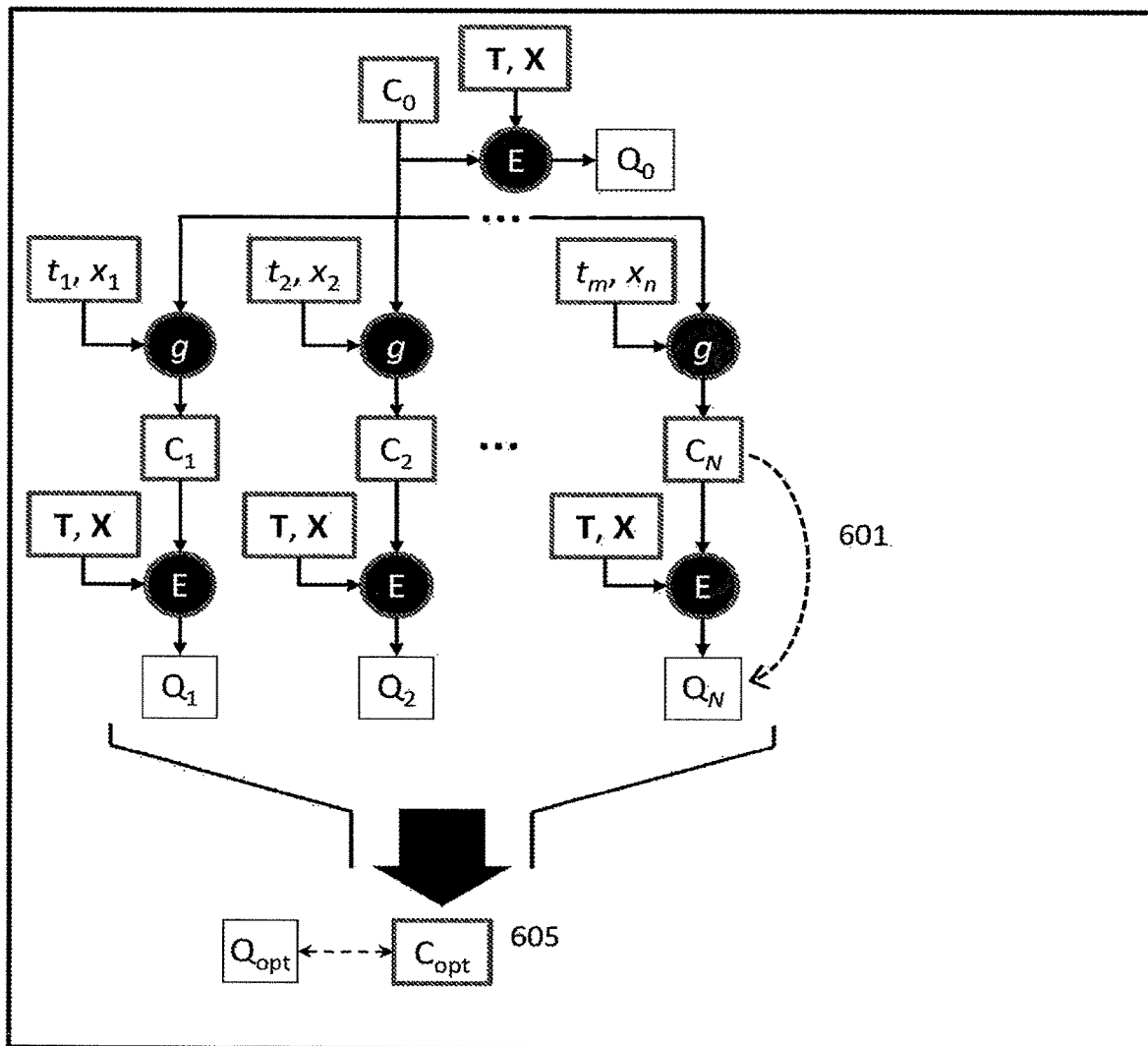
FIGS. 9(g) and 9(h) are flow charts showing a multilayer calibration.
Figure 9H:
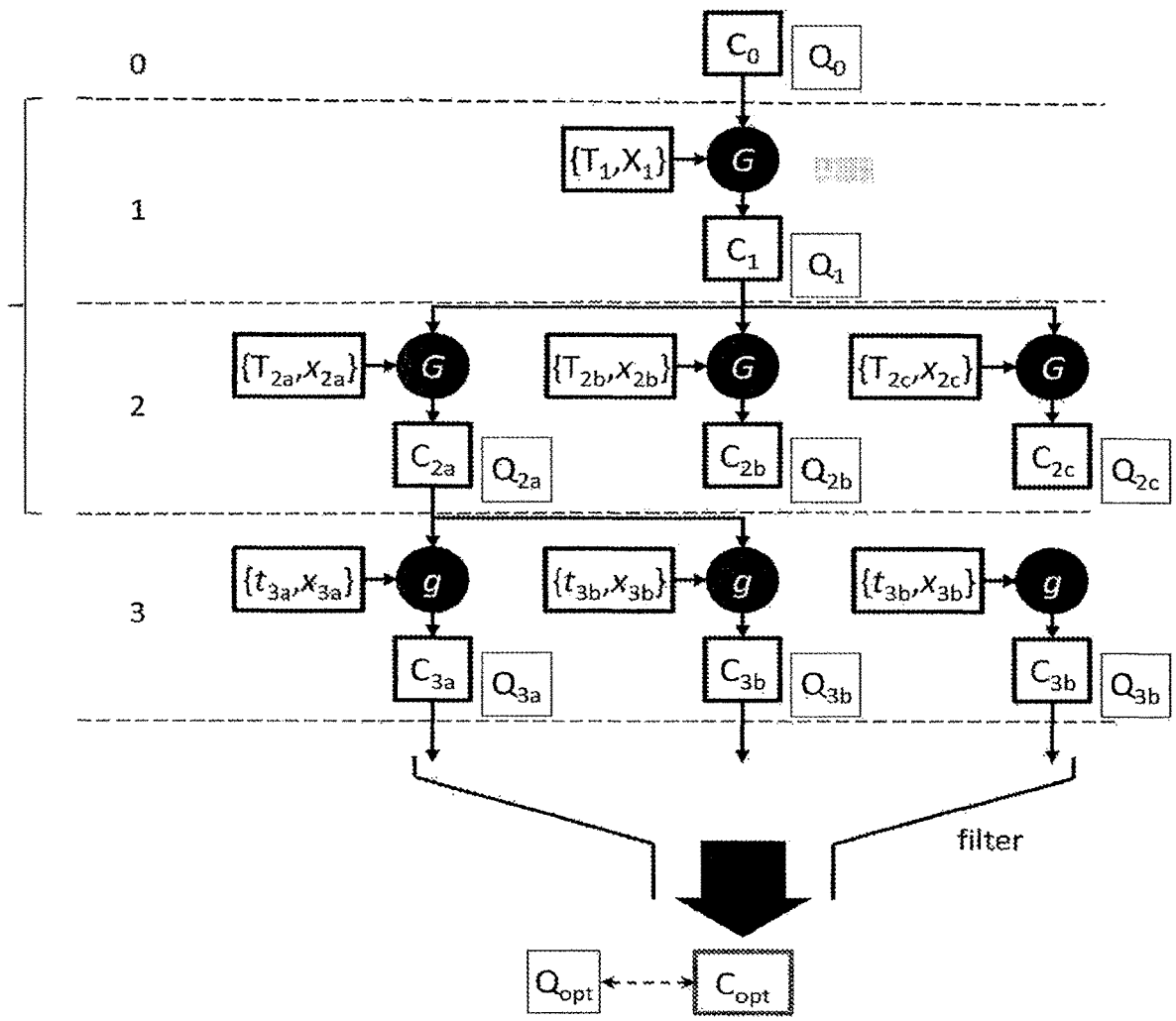
Figure 9I:
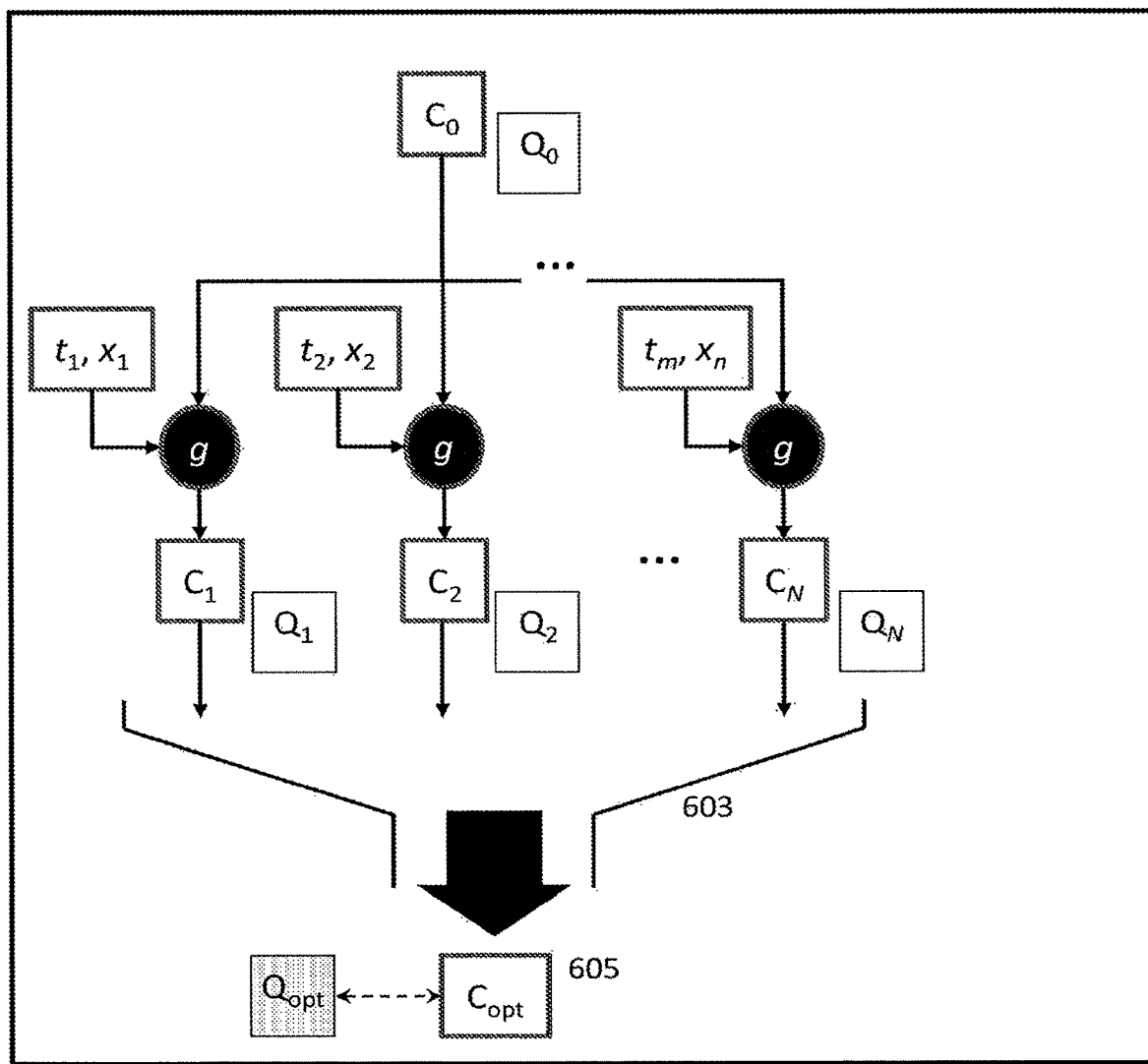
FIG. 9(i) is a flow chart showing a recursive method applied to the multilayer calibration.

FIG. 9(e) shows how the Candidate calibration $C_i$ is evaluated (through E) by comparing simulated output $\{S, P\}$ with corresponding measured data $\{T, X\}$ to produce quality metric $Q_i$ (normalised to values $\geq 1$, where smaller values indicate higher quality) and the functions of the calibration evaluator (E).

FIG. 9(*f*) shows schematically, multi-Layer Calibration Initialisation for N (≥1) coatings on substrate S.

FIGS. 9(*e*) and 9(*f*) illustrate the concepts of evaluating the quality of a given calibration as well as the relationship between single-layer calibrations and a multi-layer calibration, both of which can be generalised as a generic calibration C the solution for which can be sought using the calibration routines described here FIG. 9(*g*) is a flow chart showing the multilayer calibration using the above described method. Here, the Initial calibration $C_0$ is a single- or multi-layer calibration (S or M). All candidate calibrations C are evaluated (by calculate quality metric Q with E) that compares thicknesses produced for terahertz measurement set T with expected coating thickness set X.

As shown by the doted arrow 601, candidate calibration $C_i$ yields quality metric $Q_i$ (normalised to values≥ 1, where smaller values indicate higher quality. In step 603, candidates $C_i$ are filtered to select the optimum by find minimum quality metric $Q_i$. The optimum calibration $C_{opt}$ is that with minimum quality metric $Q_{opt}$ output at 605.

The above is also shown in condensed flow chart of FIG. 9(*h*) where in step 603, candidates $C_i$ are filtered to select the optimum by find minimum quality metric $Q_i$. The optimum calibration $C_{opt}$ is that with minimum quality metric $Q_{opt}$ output at 605.

FIG. 9(*i*) shows a variation on the calibration methods of FIGS. 9(*g*) and 9(*h*) with recursive calibration where there is recursive generation of candidate calibrations starting from initial calibration $C_0$.

At recursion level 1, generator G operates on measurement and thickness subsets $\{T_1, X_1\}$ that share the same layer-substrate structure but with different thickness combinations to generate a calibration with common optical properties. At recursion level 2, generator G operates on multiple terahertz measurements $(T_i)$ made on coated substrate that share the same thickness combination $x_i$. Each thickness combination has one or more associated measurements that produce a different candidate calibration $C_2$. At recursion level 3, generator g operates on an individual terahertz measurement t corresponding to a expected thickness combination x. Candidate calibrations are generated for each parent calibration generated at level 2. The optimum calibration $C_{opt}$ is that from recursion level 3 with minimum quality metric $Q_{opt}$.

Due to space constraints, recursion level 3 indicates only what happens to the children of parent $C_{2a}$. The other calibrations generated at level 2 ($C_{2b}$ and $C_{2c}$ as depicted here) could each generate separate child calibrations as well. Any candidate calibrations generated on level 3 are then put forward as the list of potential candidate calibrations from which the optimum calibration is selected (by filtering based on quality metric associated with each calibration). The calibrations generated at previous recursion levels (0, 1 and 2) can be considered as intermediate calibrations the children of which that are generated on subsequent levels providing an improvement on the calibrations generated at preceding levels.

The recursive calibration differs from the direct calibration of FIGS. 9(*g*) and 9(*h*) by incorporating recursion levels 1 and 2.

In summary, in the enhanced calibration, the calibration has been modified to proceed recursively and on decreasing measurement scales using grouped optimisation as explained below.

In the calibration described with reference to FIGS. 9(*g*) and 9(*h*) all trial calibrations (for a given combination of layer optical models) were generated from a single initial calibration (defined by a set of initial parameter values and optimisation search limits). Doing so omitted the possibility that the resultant calibration produced by modifying the original calibration could itself serve as a better initial calibration, from which to generate an improved calibration. The calibration routine was therefore made to be recursive with a logical limit.

In the calibration described with reference to FIGS. 9(*g*) and 9(*h*), trial calibrations were generated from an initial calibration by optimising both sample-specific parameters (those associated with the coating layer combination: thickness and optical model parameters of individual layers) and measurement-dependent parameters (surface offset and tilt factor) for one or more waveforms measured from the same location on a coated panel. Calibration generated by performing grouped optimisation, i.e. to multiple waveforms, produces a calibration in which the uncertainty on individual parameters exceeds that of a calibration generated by optimising to each waveform individually. During grouped optimisation parameters that are specific to individual measured waveforms (offset and tilt) are treated independently and the remaining (layer structure) parameters are treated as common to that group of waveforms (obtained from the same panel location).

The concept of using recursive calibration on varying measurement scales allows calibration to improve with subsequent generations (through recursion) and from an improved initial calibration (by applying grouped optimisation to measured waveforms from multiple locations, i.e. from the same coating-substrate combination but with different thickness combinations, so as to find a calibration that describes reflection from those thickness combinations) and subsequently refining child generations to have smaller parameter uncertainties by reducing the measurement scale at which optimisation is applied: from coating combination level (i.e. waveforms from multiple locations); to location level (i.e. multiple waveforms from the same location); to measurement level (i.e. individual waveforms).

Figure 10:
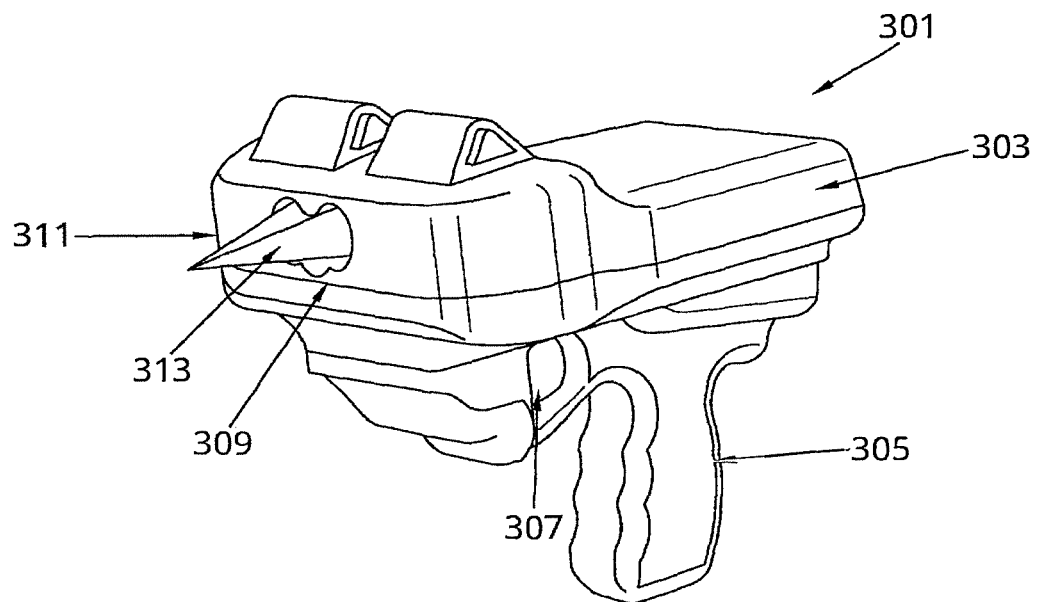
FIG. 10 is a schematic of a sensor head in accordance with an embodiment of the invention.

FIG. 10 shows a diagram of a sensor in accordance with an embodiment of the invention. The sensor 301 comprises a main body 303 with a handle 305. In the specific embodiment, the handle 305 is similar to that of a handgun and a trigger 307 is provided for activating the sensor. The sensor comprises an output port 3 with an output terahertz probe 311 and an input terahertz probe 313. The output terahertz probe emits terahertz radiation towards the sample and it is collected via the input probe.

Figure 11:
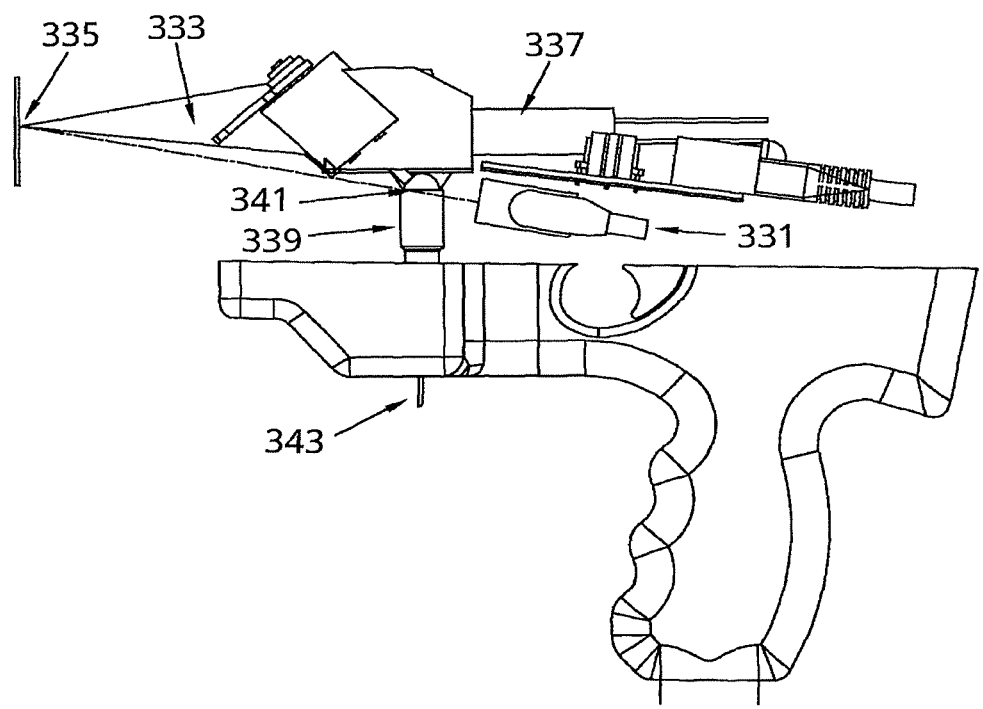
FIG. 11 is a cut-away view of the sensor head of FIG. 10.

FIG. 11 is a cut-away diagram of the sensor of FIG. 10.

A distance sensor 331 (either a laser gauge or ultrasonic gauge) is provided under A circuit board. It can be seen that the axis of this auxiliary distance sensor 331 is aligned to intersect the THz beam 333 axis at the THz focus 335. It cannot be on axis because it would intersect with the laser alignment tool.

The alignment laser 337 is a visible class II laser which is used in the manual version to roughly feedback to the user when the sensor is normal to the body.

The alignment laser 337 is a visible class II laser which is used in the manually held sensor version to roughly feedback to the user when the sensor is normal to the body. This can be done because the laser is shone through a small (~1 mm) pinhole in a metal mirror. A clearcoat layer of the sample reflects the laser back to the sensor 301, and if a slight tilt misalignment is present, the returned beam reflects from the metal mirror and returns to the paint surface, showing a second laser spot. The operator's role is to angle the sensor in such a way as to overlap the two spots. Then the sensor 301 is approximately normal to the surface. This is also used in the robotic version to initialise teach mode. Thus two alignment tools can be used in conjunction: the distance sensor for focal distance, and the alignment laser for angle.

The laser light from a core system (800 nm in this embodiment) is delivered through two fibre optical cables 343, (approximately 13 metres long for the robotic version and 7 metres for the handheld) to the sensor 301. In the sensor 301, the fibre optic cables terminate inside the THz device cartridges 339 (one emitter, one detector). In fact it is not possible to propagate THz radiation through optical fibres in this manner at all and therefore radiation of a different frequency is supplied to the THZ device cartridges 339 which then convert the radiation to THz radiation. The cartridge 339 contains a lens 341, which focusses the output from the fibre onto the photoconductive region of the semiconductor device, where the impedance of a photoconductive switch is modulated at THz frequencies, producing THz radiation.

The radiation is coupled into free space using a silicon lens 341, whence it is focused onto the sample surface using (in this embodiment) an ellipsoidal mirror. The returning THz pulse is focused by the silicon lens on the receiver cartridge 339, and generates a THz current in the receiver photoconductor. The THz signal is modulated electrically at the emitter at 33 kHz, and lock-in detection at the receiver results in a 33 kHz frequency voltage with amplitude proportional to the THz signal detected. The output is further modulated by a 15 Hz time-delay line which probes the THz signal at different points in time relative to the reference signal. The waveform is reconstructed by synchronising the receiver voltage data with the time domain positional output data.

Figure 12:
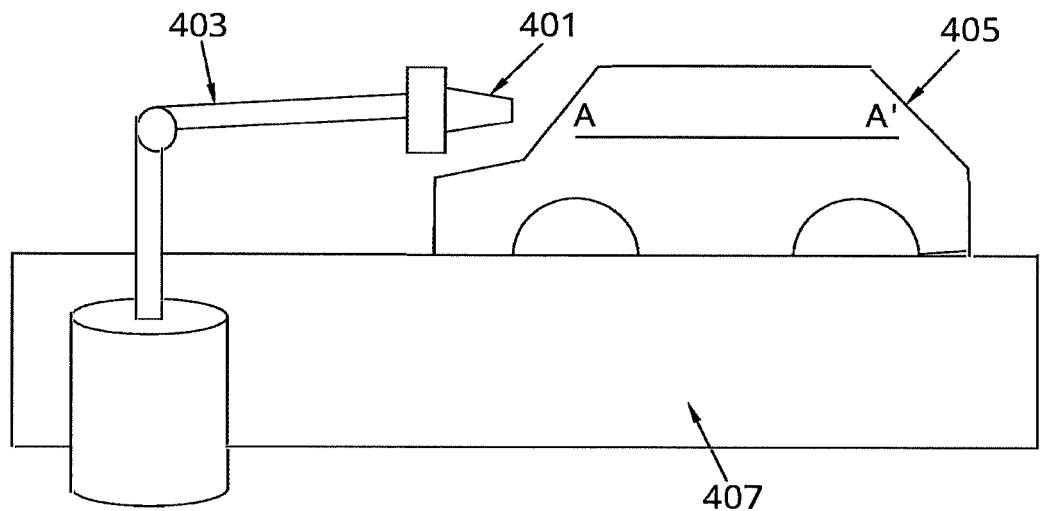
FIG. 12 is a schematic of the sensor head on a robot arm.

FIG. 12 is a basic schematic of the terahertz sensor for one provided on a robot arm 403. It will be appreciated the robot arm is purely for schematic purposes and in practice, the robot arm is likely to have many more degrees of freedom than those shown. The car body 405 to be analyzed is provided on train 407. Train 407 can move the car body from a previous processing stage, for example the painting stage towards the measurement stage with sensor 401.

In an embodiment, the sensor on the robot arm 402 can be automatically positioned. Here, a scan mode is used to place the sensor at the correct distance and orientation to the sample surface. Accurate positioning is required prior to acquisition of calibration data (as such data must be obtained with sample surface as close to normal orientation and in focus), for initial programming of robot measurement locations on the sample, especially in the case where other sensing modalities (e.g. ultrasound, vision) are known to fail (e.g. on the narrow windshield flange), and for determining robot positions at set intervals along a linear surface scan. In some implementations (e.g. where vision system is not capable of accurately re-positioning the sensor relative to the measurement locations from vehicle to vehicle) it may be necessary to run automated positioning immediately before each point measurement. Positioning the sensor such that the measured surface is at focus and normal to the direction of the terahertz beam is done by adjusting the sensor position and orientation until properties of the terahertz signal reflected from the surface (signal amplitude and offset between surface and terahertz focus) indicates that ideal orientation and position has been achieved.

Also, in a robotic system, it is possible to operate the sensor in a scan mode allows for continuous, or non-continuous, scans across a coated body. Extension of this concept provides the ability to perform two-dimensional mapping of a coated surface by running multiple side-by-side line scans. For each line scan, start and end points along the surface are defined by the operator. To ensure accurate positioning of the sensor along the entire line scan, the line is split into segments and the automated positioning (above) applied at each to determine ideal sensor positioning. Interpolation is applied to determine required robot movements at the remaining points on the line. For a continuous line scan, the robot is moved along the line without stopping while individual waveforms (i.e. without co-averaging) are acquired continuously. When the end of the line is reached data acquisition stops and, if required, processing is applied to perform some level of co-averaging between groups of neighbouring waveforms before calculating thickness along the line. For a non-continuous line scan, the robot is paused at pre-defined intervals along the line and a standard point measurement made at each location.

In an embodiment, the robotic system is provided with a set of routines for use with a robotic system to determine offsets (lateral, vertical and in orientation) between the tool centre point and the terahertz focus. Three routines consisting of a pre-programmed set of robotic movements of the sensor initially focused on a fixed reflective surface (such as the alignment plate) are considered: one to check for differences in orientation between direction of propagation of terahertz beam and the robot z-axis (by revolving the end-of-arm tool about the current definition of the z-axis); one to determine vertical offset by performing a step scan along the z-axis; and the last consisting of step scans about x- and y-axes of the tool centre point. These three scans are discussed as an example, other scan types are possible.

From properties of the measured terahertz data (signal amplitude and distance between measured surface and terahertz focus) collected at the various robot positions and orientations visited in each scan, the various offsets between the terahertz focus and the tool centre point can be determined and removed by either redefining the tool centre point or applying those offsets to the existing tool centre point definition for further movements of the robot. These routines would be used at installation of the sensor or whenever the sensor is repositioned on the end-or-arm tool, e.g. for maintenance of terahertz sensor.

Figure 13:
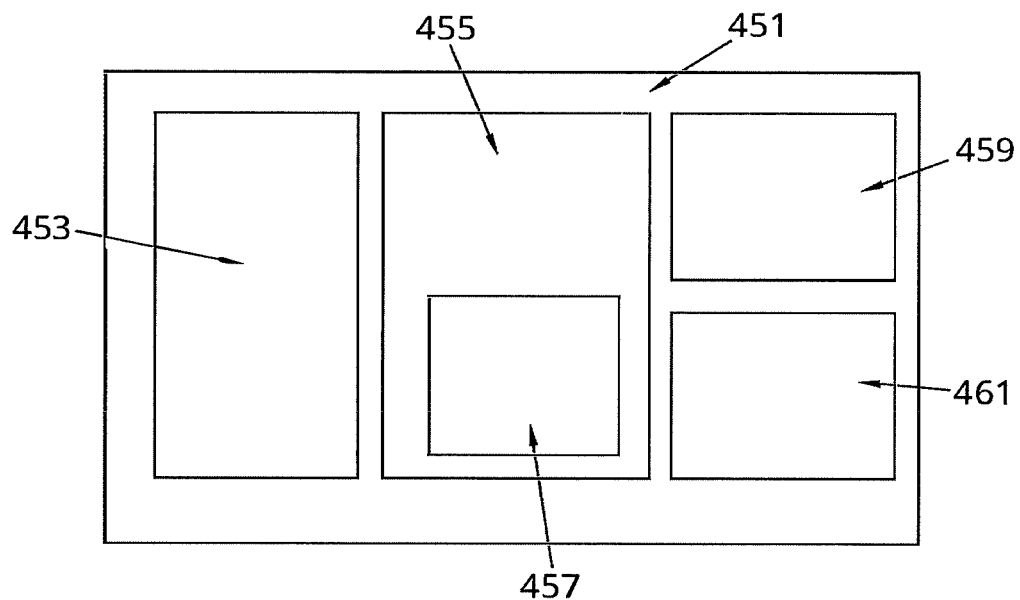
FIG. 13 is an overview of a basic analysis unit.

For completeness, a basic diagram of the analysis unit is shown in FIG. 13. The analysis unit can determine the thickness of the layers in real time or the data can be saved by the analysis unit and processed at a later time.

The analysis unit 451 which can be embodied on a standard computer comprises a memory 453, a processor 455 running a program 457 in addition there is an input module 459 and an output module 461.

In an embodiment, the input module 459 receives data from the sensor 401 the input is in the form of a time domain terahertz trace.

This data is then passed to processor 455 which runs program 457. During the calibration phase, the data that is passed to module 459 is processed by processor 455 and the estimated parameters and the trial ranges are saved to memory 453. When analyzing data from a sample, the processor 455 calls the parameters and ranges from the memory 453. The output is provided by output module 461.

In a further embodiment, the processor 455 is a multi-core processor. This allows much faster processing by calculating thicknesses in parallel using multiple cores of the PC. In an embodiment, 46 concurrent fits were achieved, but this could be extended.

In this example, the plurality of measurements are made in a batch. The fitting begins automatically as soon as all of the measurements in the batch (job) are complete. No user intervention is necessary.

Assignment of fitting threads to cores is dynamic. A new fit requirement is passed to each core as soon as it completes the previous fit, minimising the total time.

Fits 'time-out' if a problem is encountered, such that occasional bad data points do not cause bottlenecks.

In an embodiment, fit thickness results are automatically compiled, and written to an output file to form a permanent record.

In a further embodiment, the above method is used to measure the thickness of paint along a line of the vehicle or object being coated.

In FIG. 12 a diagram of a car, is shown where line A-A' shows the position of a line scan. In an embodiment, the sensor is the sensor described above in relation to FIGS. 10 and 11.

The sensor 401 is controlled by processor 455 (of FIG. 13). Processor 455 is adapted to learn the shape and then control the sensor to move in a line along the shape following the contours of the shape such that the sensor remains a known distance from the shape.

This control can be achieved using a CAD package or similar software.

In one embodiment, the system just measures the thickness at each point in the way previously described. However, in a further embodiment, an additional constraint is provided on the fitting of the thickness in that the thickness of adjacent points must vary in a continuous manner. Thus the thickness fitting of each point is no longer independent, but depends on the thicknesses of the surrounding points.

There are a number of computational routes to producing continuous thickness data. One such embodiment is as follows. Prior to the line scan beginning, a pre-scan routine is executed which makes conventional, discrete measurements at a number of specified points along the line scan trajectory. These include measurements at:

The beginning of the line scan

At discrete 'waypoints' at intervals specified by the user, but typically at 100 to 500 mm intervals, depending upon the robot speed and curvature of the surface.

The end of the line scan

These points are batch fitted at the end of the pre-scan, to give individual thickness readings. They also contain information regarding the alignment of the head: specifically any deviation from focus.

The output of the pre-scan is used to fine tune the actual line-scan in two ways:

Correcting the focal distance by interpolation of deviations measured at each waypoint, feeding back to the robot controller.

'Seeding' the thickness calculations by returning thicknesses and refractive index values at each point.

The line scan is then measured, using a waveform rate of typically 7.5 Hz to 30 Hz, and robot speeds of typically 10 to 200 mm per second. This yields point spacings along the car body of between 0.3 mm and 26 mm, as required.

Each interval between adjacent waypoints is passed to a separate core for processing. Thus each interval can be fitted simultaneously.

The solver begins with the first (known) point, and calculates the adjacent point, making two assumptions:

That the refractive index of the layers does not appreciably change between points.

That the thickness of the paint layers changes only by a maximum value, which depends upon the lateral distance between points, such that the gradient (thickness change per unit lateral distance) is constrained to a set maximum value, specific to a particular calibration and determined experimentally.

The process is then sequential, using the first point to calculate the second, and then the second to calculate the third, and so on.

The process can be generalised to 2D surfaces by using a pre-scan to cover the area with intervals both horizontally and vertically, thus defining an area of polygons.

In an embodiment, the linear robot motion path across the panel is defined using vehicle body CAD files and subsequently modified for individual vehicle and panel positioning using a vision system and terahertz alignment scan mode.

A measurement program then triggers terahertz waveform acquisition at beginning of the linear path, after which terahertz measurements are made at regular time intervals until the end of the linear path is reached at which point terahertz measurement is stopped.

Coating thickness calculation is done using batch-fitting and thickness values can be displayed on-screen and/or recorded in an output data file.

In a further embodiment, the above 1D line scan is extended to a 2D area scan. This can provide dense 2-D mapping of individual vehicle body panels.

The above line scan and 2D area scan can be used to provide feedback to an operator that will allow for improvements in robot paint paths so as to optimise paint thickness uniformity across individual panels and to reduce colour matching problems between adjacent panels.

The following descriptions are workflows in accordance with an embodiment:

Multi-Point Measurement Job Using Handheld/Robotic System

1) At system start-up (e.g. at start of shift) operator launches software, which performs initialisation routine: switches on laser, centres delay line, checks signal quality. For robotic inspection cell, system remains in standby mode when not in use (with laser switched off, and control software open). The pre-sets for this routine are stored in memory 453 and are performed under the control of processor 457.

2) Vehicle (of a particular colour and body style) enters the manual/robotic inspection bay 3) A new job file is created in software (manually by the operator or as a step in the automated program), which clears the contents of any previous job (measurements and selected calibration(s)).

4) Vehicle body style and colour of current vehicle are provided by the VIN on each vehicle. The measurement job list appropriate to the body style and the calibration(s) appropriate to the vehicle colour(s) and substrate(s) are selected from the list of available customer specific options which are pre-stored in the memory. Pre-defined calibrations and job lists are stored on the system PC that can be accessed through the software. A job refers to the set of measurements made at various, pre-defined locations on the vehicle body. The job list specifies how the measurements at each location on the vehicle body are named in the job measurement file. Furthermore, the job list may also specify a number of repeat measurements to be made at each location, as well as the coating-substrate combination at each location, so that the calibration can be automatically selected depending on a particular panel location (e.g. a vehicle body may consist of panels with different substrates, paint combinations and expected coating thicknesses).
5) For handheld system, operator starts live streaming of terahertz waveforms.
6) The sensor is moved (by operator/robot) to the location associated with the first measurement in the job list.
7) The sensor position is adjusted until a suitable position relative to the coated surface in which to acquire measurements of sufficiently high quality is achieved, i.e. with the surface in focus of the terahertz beam and with the surface normal to the direction of propagation of the beam.
   a robotic system will not necessarily change sensor position from the pre-programmed position. A vision system will ensure that the sensor is re-positioned to within given tolerances on every vehicle, independent of the particular orientation and position of each vehicle. An automated positioning routine is however provided for the purpose of both programming robot positions and for further adjustment if and when necessary: for measurement on the windshield flange; for determining optimum position at regular intervals along a surface line scan and to ensure optimal positioning for measurement of calibration samples.
   the handheld sensor provides real-time audio-visual feedback (using a combination of ultrasonic distance gauge and information from the continuously streamed terahertz signal) to the operator to indicate both how to achieve optimum positioning and to indicate when suitable positioning has been achieved and is maintained over the duration of data acquisition at a given measurement location.
8) When the sensor has been suitably positioned relative to the coated surface, data acquisition is begun (via a depressible trigger in the case of the handheld sensor) or automatically by the robot control logic. Should sensor position become unsuitable during data acquisition, the operator is informed via real-time audio-visual feedback and data acquisition is automatically paused until the sensor has been suitably repositioned.
9) The measured data is appended to the current measurement file and labelled according to the name provided in the job list.
10) Depending on user preferences, coating thickness calculation will begin immediately after data acquisition at the current location has finished. This behavior can be enabled or disabled at any point during the measurement job, e.g. allowing for inspection of coating thickness at the start of a job and continuing thereafter without thickness calculation.
11) The sensor is moved to the next location on the vehicle body and steps 7 to 10 repeated until measurements have been obtained at all locations in the job list (if one was supplied).
12) If a job list was supplied and the end of that list has been reached, the terahertz beam is switched off (automatically or manually by the operator).
13) For any measurements for which thickness was not calculated immediately after data acquisition, thickness calculation is applied automatically to all remaining measurements contained in the measurement file. No operator input is required (or even permitted) for thickness calculation.
14) Calculated coating thickness values for the current job are (manually/automatically) exported to a human readable and/or a machine readable output file.
15) The results of thickness calculations are cleared before terahertz measurements and the selected calibration(s) are stored to file for quality assurance and traceability purposes.

The above workflow relates to sample measurement. The next workflow relates to Calibration Measurement (Handheld system)
1) Prepare sets of calibration panels: single-layer panels and multi-layer panels (one set per colour).
2) For each single-layer panel use a total thickness gauge (eddy current/magnetic gauge, e.g. Elcometer) to identify the location on panel where the coating layer is thickest and mark that point (with a circle so that terahertz readings can be obtained inside that circle). Similarly, for each multi-layer panel, mark a circle at the centre of each panel where terahertz readings will be taken and where independent means (ideally optical microscopy) will be used to determine the thickness of the individual coatings at the same location.
3) Prepare job list files specifying measurement names for all measurement locations on each panel (in both the single-layer and multi-layer panel sets), including the number of repeat measurements (e.g. three) to be made at each location.
4) Launch TeraCota software. Initialisation procedure will run and default calibration (a zero-thickness layer of air on metal substrate) automatically selected and 'calculate thickness after measurement' button disabled. Start terahertz beam.
5) Attach focal plane aperture to handheld sensor head
6) Take one of the panel sets (single-layer or one of the multi-layer panel sets) and select the corresponding job list file, which will populate the user interface with the measurement names to be acquired for the given panel set.
7) Place a panel on an alignment plate with coated side facing up and lower the focal plane aperture onto the coated surface.
8) Position the panel beneath the aperture, the centre of which corresponds to the focus of the emitted terahertz beam, such that the centre of the circular marker coincides with the centre of the aperture, taking care not to scratch the surface of the coating when moving the panel.
9) Ensure sensor is held in place on top of the coated panel (either by clamping in place or by applying downward pressure)
10) Take a point measurement
11) Repeat step 10 until the desired number of repeat measurements, as specified by the job list file, have been acquired.
12) Repeat steps 8 to 11 for any additional locations on the panel 13) Repeat steps 7 to 12 for all remaining panels in the set.
14) Stop terahertz beam and save current file, before creating a new blank measurement file
15) Repeat steps 6 to 14 for all remaining panel sets Calibration Measurement Workflow (Robotic System)
The is similar to the above, except in how the sensor is positioned and panels are placed.
The robot moves the sensor to a pre-programmed location above the centre of an alignment plate that is fixed in place in the robotic inspection cell.

Each panel is sat on top of the alignment plate with its marked circular region of interest aligned with the pre-programmed location Automated sensor positioning is used to improve sensor position (distance and orientation) relative to each coated panel Generation of Calibration File(s) from Calibration Measurements The procedure for analysis of the calibration data in order to generate calibration files that can be subsequently stored in the memory 453 and then loaded and applied to measurement data is as follows. The process is independent of whether the data was acquired on a handheld or robotic system. Indeed, it is not necessary to use the same system for data acquisition and analysis.

Auto Paint Sample Calibration Method—Single Layer

1. Set a destination folder for the calibration measurements.
2. Open the application 457, possible by double clicking on the desktop icon.
3. Load the waveforms from which the single layer calibrations shall be taken.
4. At this stage, it is possible for the used to select various options, for example 'Model' select 'Advanced Model Options':
   a. select 'Layer Configuration', select 'Single Layer'.
   b. Select 'Filtering Methods' tab, select 'Experimental Reference' from drop-down menu.
   c. Select 'Optical Parameters' tab, check that the 'Angle' is set to 12.
   d. Select 'Scaling Parameters' tab, check both 'Fit' boxes and both 'Use limits' boxes. Set 'Phase Offset' to −5.0, 5.0.
5. From 'Layer Setup' on right, select 'generic1' from the 'LAYER 1' list.
6. Input values into 'Calibration Thickness and Limits' and into the upper and lower limit (+/−5), on the bottom right of the screen.
7. Press 'Reset to Calibration Thickness' button (centre of the right hand side panel).
8. Make sure to change 'Name' for each structure (top of 'Layer Setup' panel). This will be the name given to the new structure.
9. Press 'Add to Document'. This will create a new structure with the name entered above.
10. Select the newly created structure from the pull down menu in the 'Target' tab.
11. Within 'Calibration', press 'Single Layer Expected Thickness', enter values for Thickness and Range, close window.
12. Select proper data (waveform) from list on left, to be the input to the calibration. The selected waveform should appear in the centre graph window.
13. Within 'Calibration', select 'Perform Single Layer Calibration'.
14. When calibration finishes, name the file, save to selected folder (saves 6 files).

Auto Paint Sample Calibration Method—Multi-Layer

1. Retrieve the Multi-Layer measurement file from the memory.
2. Within 'Model', select 'Advanced Model Options':
   a. Select 'Filter Method', select 'Experimental Reference'.
   b. Within 'Model', select 'Optical Parameters', set 'Angle' to 12.
   c. Within 'Model', select 'Scaling Parameters', make sure both 'Fit' boxes are checked, uncheck both 'Use Limits' boxes, make sure defaults are set to zero for 'Offset' and one for 'Tilt'.
3. In 'Configurations', select correct number of layers for the multilayer calibration measurements.
4. Import Single Layer Calibrations: Within 'File', select 'Import Material Calibrations' (.csv files), create new destination folder for multi-layer calibration structure, copy (.csv) summary files for each single layer into newly created folder, select (.csv) files from new folder and import into TeraCota software.
5. Using Drop-Down menus it is possible to set different types of layers, for example: set 'Layer 1' to clearcoat, 'Layer 2' to basecoat, 'Layer 3' to primer, 'Layer 4' to electrocoat, and 'Substrate' to 'perfect metal'.
6. Set the refractive indices in each of the 'Layer' tabs, must choose Drude-Lorentz or Debye2 model for each layer: whichever gives the best fit in each case.
7. Change 'Name' of multi-layer structure to reflect current measurement.
8. Under each 'Layer' tab:
   a. Press 'Reset to Calibration Thickness' to update values.
   b. Press 'Toggle Fit' to check all 'Fit' boxes.
   c. Uncheck all 'Use Limits' boxes.
9. Press 'Add to Document'.
10. Within 'Calibrations', press 'Prepare Multilayer Calibration Table':
    a. In Dropdown menu, press 'Select Input Structure', select the structure that was just created.
    b. Enter the 'Target Thickness' (defaults are generated from single layer calculations: these should be replaced with the target thicknesses for the measurements on which the resulting calibration will be applied).
    c. Enable all data sets that are to be used in calibration, check 'True' and 'False' boxes in table.
    d. Enter readings for individual thicknesses into 'Known Layer Thicknesses' columns.
    e. Enter total thickness into 'Known Total Thickness', otherwise column will generate the total automatically from inputted values. This thickness can be performed by the elcometer.
    f. Press 'Validate', should display 'Valid'
    g. Press 'Start' to begin calibration
11. When calibration finishes, the file generated in 'Structures' folder is named after one of the files used to run the calibration, this file will be renamed to the appropriate multi-layer sample.

The above embodiments allow the problem of modelling a THz waveform to be simplified if the dimension and size of the solution space to be explored (by least squares minimisation) can be reduced, by applying constraints (and/or upper and lower bounds) on the possible values for the unknown quantities (thickness and refractive index). The problem of calculating individual coating thickness is greatly reduced if the optical response (refractive index) of all coatings and substrate are known in advance. Thus given the optical properties (a constrained, but not necessarily fixed, refractive index) of each coating and the measured reflected signal, the thickness of individual coating layers can be calculated using a local optimisation routine to minimize the difference between the measured and simulated signals.

The invention claimed is:

1. A method for determining the thickness of a plurality of coating layers, the method comprising:
   performing an analysis on calibration data to determine initial values and search limits of optical parameters of said plurality of coating layers;
   irradiating the said plurality of layers with a pulse of THz radiation, said pulse comprising a plurality of frequencies in the range from 0.01 THz to 10 THz;
   detecting the reflected radiation to produce a sample response, said sample response being derived from the reflected radiation;
   producing a synthesised waveform using the optical parameters and predetermined initial thicknesses of said layers;
   comparing said synthesised waveform with said sample response;
   varying said thicknesses and varying said optical parameters within the said search limits to minimise an error measured between the sample response and the synthesised waveform; and
   outputting the thicknesses of the layers.

2. A method according to claim 1, wherein the analysis is capable of determining that the search limits of one or more of the optical parameters are zero.

3. A method according to claim 1, wherein the analysis comprises selecting preferred refractive index models from data from a first set of calibration samples and determining initial values and search limits of optical parameters from data from a second set of one or more calibration samples.

4. A method according to claim 3, wherein the first set of calibration samples are samples with a substrate and a single coating layer and the second set of calibration samples have a substrate and the said plurality of coating layers.

5. A method according to claim 4, wherein the said plurality of coating layers are provided on an object and the second set of calibration samples are areas of the said object different from the area where the THz radiation is used to measure the said plurality of coating layers.

6. A method according to claim 4, wherein the analysis further comprises performing non-THz measurements to determine an expected thickness range of the layers of the first and second set of calibration samples and determining initial estimates and initial search limits of the optical parameters from THz data and expected thickness data for the first set of calibration samples;
   wherein determining initial values and search limits of optical parameters from data from the second set uses a selected preferred refractive index model and the initial estimates and initial search limits of the optical parameters from analysis of the first set, together with expected thicknesses, wherein the thickness of layers are allowed to vary over ranges that are determined by the non-THz thickness measurements.

7. A method according to claim 3, further comprising measuring a set of calibration samples using THz radiation in the range 0.01 THz to 10 THz, and making a time domain measurement of the reflected radiation to produce said data.

8. A method according to claim 3, wherein the analysis comprises receiving calibration data comprising a time domain measurement of THz radiation in the range 0.01 THz to 10 THz reflected from the said calibration samples and fitting a synthesised waveform to said data.

9. A method according to claim 8, wherein for the second set of calibration samples, the fitting parameters for the synthesised waveform comprise the optical parameters and the thickness of the layers.

10. A method according to claim 8, wherein the output of the fitting of the calibration data of the first samples comprises a ranked list of the refractive models.

11. A method according to claim 10, wherein for the second set of calibration samples, the first ranked refractive model is used to fit the second calibration data, and wherein if this model produces poor results, the next refractive model from the ranked list is selected.

12. A method according to claim 1, wherein the sample response is derived from a reflected waveform by deconvolving the reflected waveform with an instrument response, wherein the instrument response is a measurement of the contribution of sensor components used to measure the reflected waveform.

13. A method according to claim 12, wherein the instrument response is determined from the THz signal reflected from a mirror to produce a reference signal.

14. A method according to claim 13, wherein the mirror is a movable mirror provided in the path of the THz beam before the focus of the THz beam, the method further comprising applying a scaling function to the instrument response measured using the movable mirror in order to mimic the instrument response as if measured by a mirror placed at the focus.

15. A method according to claim 14, further comprising deriving the scaling function by measuring the instrument response using a mirror positioned at the focus and comparing this with the instrument response using the movable mirror.

16. A method according to claim 1, wherein a reflected waveform is measured using a sensor, the method further comprising positioning the sensor with a measurement gauge to determine if the sensor is at a distance from the plurality of layers to allow a measurement to be performed.

17. A method according to claim 1, wherein a reflected waveform is measured using a sensor, the method further comprising aligning the sensor with an angular measuring gauge to determine if the angle of the sensor is sufficient to allow a measurement to be performed.

18. A method according to claim 1, wherein the outputting of the thickness data is performed after one or more locations on said plurality of layers have been measured.

19. A method according to claim 1, wherein the calibration data is obtained from one or more coating layers from one or more samples.

20. A system for determining the thickness of a plurality of coating layers, the system comprising:
   a sensor, said sensor comprising:
   a pulsed source of THz radiation adapted to irradiate a sample comprising said plurality of layers with a pulse of THz radiation, said pulse comprising a plurality of frequencies in the range from 0.01 THz to 10 THz; and
   a detector for detecting the reflected radiation to produce a sample response, said sample response being derived from the reflected radiation,
   the system further comprising an analysis unit, said analysis unit comprising a processor and a memory, said processor being adapted to:
   receive data describing the reflected radiation and sample response;
   access calibration data from said memory, said calibration data comprising initial values and search limits of optical parameters of said plurality of coating layers,
   produce a synthesised waveform using the optical parameters and predetermined initial thicknesses of said layers;

compare said synthesised waveform with said sample response;

vary said thicknesses and vary said optical parameters within the said search limits to minimise an error measured between the sample response and the synthesised waveform; and output the thicknesses of the layers.

21. A system according to claim 20, said system being further adapted to produce said calibration data, wherein said processor is adapted to receive first calibration data and second calibration data, said first calibration data comprising reflected THz waveforms from a first set of calibration samples and said second set of calibration data comprising reflected THz waveforms from a second set of one or more calibration samples, the first set of calibration samples are samples with a substrate and a single coating layer and the second set of one or more calibration samples have a substrate and a plurality of coating layers, the processor being adapted to select preferred refractive index models from data from a first set of calibration samples and determining initial values and search limits of optical parameters from data from the second set of one or more calibration samples.

22. A system according to claim 20, wherein the calibration data is obtained from one or more coating layers from one or more samples.

* * * * *